(12) United States Patent
Ushikura et al.

(10) Patent No.: US 11,802,981 B2
(45) Date of Patent: Oct. 31, 2023

(54) METHOD OF MANUFACTURING RADIATION DETECTOR AND RADIOGRAPHIC IMAGING APPARATUS

(71) Applicant: FUJIFILM CORPORATION, Tokyo (JP)

(72) Inventors: Shinichi Ushikura, Kanagawa (JP); Munetaka Kato, Kanagawa (JP); Keiichi Akamatsu, Kanagawa (JP); Haruyasu Nakatsugawa, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 197 days.

(21) Appl. No.: 17/394,407

(22) Filed: Aug. 5, 2021

(65) Prior Publication Data

US 2021/0364658 A1    Nov. 25, 2021

Related U.S. Application Data

(63) Continuation of application No. PCT/JP2020/005114, filed on Feb. 10, 2020.

(30) Foreign Application Priority Data

Feb. 8, 2019    (JP) ................................. 2019-022119

(51) Int. Cl.
*G01T 1/202* (2006.01)
*A61B 6/00* (2006.01)
*H01L 27/146* (2006.01)

(52) U.S. Cl.
CPC ................ *G01T 1/202* (2013.01); *A61B 6/00* (2013.01); *H01L 27/14658* (2013.01); *H01L 27/14689* (2013.01)

(58) Field of Classification Search
None
See application file for complete search history.

(56) References Cited

U.S. PATENT DOCUMENTS

2003/0209652 A1* 11/2003 Fujii ................ H01L 27/14634
                                                              250/214.1
2012/0217407 A1    8/2012 Iwakiri et al.
(Continued)

FOREIGN PATENT DOCUMENTS

CN          107742628 A    2/2018
JP          2003-270352 A    9/2003
(Continued)

OTHER PUBLICATIONS

English language translation of the following: Office action dated Nov. 2, 2021, from the JPO in a Japanese patent application No. 2020-571318 corresponding to the instant patent application.
(Continued)

*Primary Examiner* — Edwin C Gunberg
(74) *Attorney, Agent, or Firm* — SOLARIS Intellectual Property Group, PLLC

(57) ABSTRACT

A method of manufacturing a radiation detector includes: forming a substrate in which a flexible base material is provided via a peeling layer on a support body and plural pixels that accumulate electric charges generated in response to light converted from radiation are provided in a pixel region of the base material; forming a conversion layer for converting the radiation into light on a surface of the base material; providing a first reinforcing substrate on a surface of the conversion layer opposite to a surface on the substrate side; peeling the substrate provided with the conversion layer and the first reinforcing substrate from the support body; providing a second reinforcing substrate on a surface of the substrate peeled from the support body; and peeling
(Continued)

the first reinforcing substrate from the substrate provided with the conversion layer after providing the second reinforcing substrate.

22 Claims, 19 Drawing Sheets

(56) References Cited

U.S. PATENT DOCUMENTS

| | | | |
|---|---|---|---|
| 2012/0219114 | A1 | 8/2012 | Iwakiri et al. |
| 2019/0131027 | A1 | 5/2019 | Fujioka et al. |

FOREIGN PATENT DOCUMENTS

| | | | |
|---|---|---|---|
| JP | 2007-324502 | A | 12/2007 |
| JP | 2009-133837 | A | 6/2009 |
| JP | 2012-013572 | A | 1/2012 |
| JP | 2012-112725 | A | 6/2012 |
| JP | 2012-173275 | A | 9/2012 |
| JP | 2012-177624 | A | 9/2012 |
| JP | 2016-070890 | A | 5/2016 |
| TW | 2017-43121 | A | 12/2017 |

OTHER PUBLICATIONS

International Search Report issued in International Application No. PCT/JP2020/005114 dated Apr. 14, 2020.

Written Opinion of the ISA issued in International Application No. PCT/JP2020/005114 dated Apr. 14, 2020.

English language translation of the following: Office action dated Jul. 4, 2023 from the TIPO in a Taiwan patent application No. 109103972 corresponding to the instant patent application. The office action translation is submitted now in order to supplement the understanding of the cited references which are being disclosed in the instant Information Disclosure Statement.

* cited by examiner

METHOD OF MANUFACTURING RADIATION DETECTOR AND RADIOGRAPHIC IMAGING APPARATUS

CROSS-REFERENCE TO RELATED APPLICATIONS

This application is a continuation application of International Application No. PCT/JP2020/005114, filed on Feb. 10, 2020, which is incorporated herein by reference in its entirety. Further, this application claims priority from Japanese Patent Application No. 2019-022119, filed on Feb. 8, 2019, the disclosure of which is incorporated by reference herein in its entirety.

BACKGROUND

1. Technical Field

The present disclosure relates to a method of manufacturing a radiation detector and a radiographic imaging apparatus.

2. Description of the Related Art

In the related art, radiographic imaging apparatuses that perform radiographic imaging for medical diagnosis have been known. A radiation detector for detecting radiation transmitted through a subject and generating a radiographic image is used for such radiographic imaging apparatuses (For example, refer to JP2009-133837A and JP2012-112725A).

As this type of radiation detector, there is one comprising a conversion layer, such as a scintillator, which converts radiation into light, and a substrate in which a plurality of pixels, which accumulate electric charges generated in response to light converted in the conversion layer, are provided in a pixel region of a base material. A flexible base material is known as the base material of the substrate of such a radiation detector, and a cable used for reading out the electric charges accumulated in the pixels is connected to the flexible base material. By using the flexible base material, for example, the weight of the radiographic imaging apparatuses (radiation detector) can be reduced, and a subject may be easily imaged.

SUMMARY

In the middle of a manufacturing process of the radiographic imaging apparatus using the flexible base material, there were concerns that a defect occurs in the substrate of the radiation detector such that the conversion layer may be peeled from the substrate or the pixels may be damaged due to the influence of deflection of the flexible base material.

Meanwhile, in a technique described in JP2009-133837A, a flexible support body that covers a conversion layer is provided on the surface of the conversion layer facing a substrate side. Additionally, in a technique described in JP2012-112725A, a resist covering a conversion layer and pixels is provided in order to protect the conversion layer and the pixels during a manufacturing process. However, in the techniques described in JP2009-133837A and JP2012-112725A, a case where the base material of the radiation detector is deflected is not sufficiently considered, and it cannot be said that it is sufficient to suppress that a defect occurs in the substrate. For that reason, in the flexible support body in JP2009-133837A and the resist in JP2012-112725A, there was a concern that the defect in the substrate caused by the deflection of the base material during the manufacture of the radiation detector could not be sufficiently suppressed.

Additionally, there is a case where it is necessary to rework a cable due to poor connection of the cable connected to the base material, or the like. In a state in which the reinforcing substrate is provided on the conversion layer side of the substrate, there is a case where the reinforcing substrate is an obstacle in a case where reworking is performed, and a peeling property in a reworking process may deteriorate.

The present disclosure provides a method of manufacturing a radiation detector and a radiographic imaging apparatus that are capable of suppressing that a defect occurs in the substrate and have an excellent peeling property in the reworking process.

Additionally, a method of manufacturing a radiation detector of a first aspect of the present disclosure comprises forming a substrate in which a flexible base material is provided via a peeling layer on a support body and a plurality of pixels that accumulate electric charges generated in response to light converted from radiation are provided in a pixel region of the base material; forming a conversion layer for converting the radiation into light on a surface of the base material provided with the pixels; providing a first reinforcing substrate on a surface of the conversion layer opposite to a surface on the substrate side; peeling the substrate provided with the conversion layer and the first reinforcing substrate from the support body; providing a second reinforcing substrate on a surface of the substrate peeled from the support body, the substrate being peeled from the support body; and peeling the first reinforcing substrate from the substrate provided with the conversion layer after providing the second reinforcing substrate.

The method of manufacturing a radiation detector according to a second aspect of the present disclosure based on the method of manufacturing the radiation detector according to the first aspect further comprises connecting one end of a flexible wiring line connected to a circuit unit for reading out the electric charges accumulated in the plurality of pixels to a terminal region of the substrate before peeling the substrate from the support body.

The method of manufacturing a radiation detector according to a third aspect of the present disclosure based on the method of manufacturing the radiation detector according to the first aspect further comprises connecting one end of a flexible wiring line connected to a circuit unit for reading out the electric charges accumulated in the plurality of pixels to a terminal region of the substrate before providing the first reinforcing substrate.

The method of manufacturing a radiation detector according to a fourth aspect of the present disclosure based on the method of manufacturing the radiation detector according to the second aspect further comprises reworking the wiring line in a state in which the support body or the second reinforcing substrate is provided in a case where a defect occurs in at least one of the wiring line or the circuit unit.

In the method of manufacturing a radiation detector according to a fifth aspect of the present disclosure based on the method of manufacturing the radiation detector according to the first aspect, a size of a surface of the first reinforcing substrate on the conversion layer side is smaller than a size of a surface of the base material provided with the pixels.

In the method of manufacturing a radiation detector according to a sixth aspect of the present disclosure based on the method of manufacturing the radiation detector according to the first aspect, a terminal region of the substrate includes a first region covered with the first reinforcing substrate and a second region not covered with the first reinforcing substrate.

In the method of manufacturing a radiation detector according to a seventh aspect of the present disclosure based on the method of manufacturing the radiation detector according to the sixth aspect, the first region is smaller than the second region.

In the method of manufacturing a radiation detector according to an eighth aspect of the present disclosure based on the method of manufacturing the radiation detector according to the sixth aspect, a length from one end part of the base material on an inner side to the other end part of the base material on an outer edge side in the first region is ¼ or less of a length from one end part of the base material on the inner side to the other end part of the base material on the outer edge side in the terminal region.

In the method of manufacturing a radiation detector according to a ninth aspect of the present disclosure based on the method of manufacturing a radiation detector according to the first aspect, the first reinforcing substrate is provided with a cutout part at a position corresponding to the terminal region of the substrate.

The method of manufacturing a radiation detector according to a tenth aspect of the present disclosure based on the method of manufacturing the radiation detector according to the first aspect further comprises connecting one end of a flexible wiring line connected to a circuit unit for reading out the electric charges accumulated in the plurality of pixels to a terminal region of the substrate after providing the second reinforcing substrate.

In the method of manufacturing a radiation detector according to an eleventh aspect of the present disclosure based on the method of manufacturing the radiation detector according to the first aspect, in peeling the substrate from the support body, the substrate is deflected and peeled from the support body.

In the method of manufacturing a radiation detector according to a twelfth aspect of the present disclosure based on the method of manufacturing the radiation detector according to the first aspect, in providing the first reinforcing substrate, the first reinforcing substrate is provided by adhering with a dismantleable adhesive of which adhesiveness is lost by radiation of ultraviolet rays, and in peeling the first reinforcing substrate, the first reinforcing substrate is peeled by radiating ultraviolet rays from a surface of the first reinforcing substrate opposite to a surface on the conversion layer side.

In the method of manufacturing a radiation detector according to a thirteenth aspect of the present disclosure based on the method of manufacturing the radiation detector according to the first aspect, a thickness of the first reinforcing substrate is smaller than a thickness of the second reinforcing substrate.

In the method of manufacturing a radiation detector according to a fourteenth aspect of the present disclosure based on the method of manufacturing the radiation detector according to the first aspect, the second reinforcing substrate has a higher stiffness than the base material.

In the method of manufacturing a radiation detector according to a fifteenth aspect of the present disclosure based on the method of manufacturing the radiation detector according to the first aspect, the second reinforcing substrate is a reinforcing substrate formed of a material having a bending modulus of elasticity of 1000 MPa or more and 2500 MPa or less.

In the method of manufacturing a radiation detector according to a sixteenth aspect of the present disclosure based on the method of manufacturing the radiation detector according to the first aspect, the second reinforcing substrate has a bending stiffness of 540 $Pacm^4$ or more and 140,000 $Pacm^4$ or less.

In the method of manufacturing a radiation detector according to a seventeenth aspect of the present disclosure based on the method of manufacturing the radiation detector according to the first aspect, a bending stiffness of the second reinforcing substrate is 100 times or more a bending stiffness of the base material.

In the method of manufacturing a radiation detector according to an eighteenth aspect of the present disclosure based on the method of manufacturing the radiation detector according to the first aspect, a ratio of a coefficient of thermal expansion of the second reinforcing substrate to a coefficient of thermal expansion of the conversion layer is 0.5 or more and 2 or less.

In the method of manufacturing a radiation detector according to a nineteenth aspect of the present disclosure based on the method of manufacturing the radiation detector according to any one of the first to twenty-sixth aspects, a size of a surface of the base material facing the second reinforcing substrate is larger than a size of a surface of the second reinforcing substrate facing the base material.

In the method of manufacturing a radiation detector according to a twentieth aspect of the present disclosure based on the method of manufacturing the radiation detector according to any one of the first to twenty-sixth aspects, the second reinforcing substrate has a plurality of layers laminated in a lamination direction to be laminated on the substrate, and a size of some of the plurality of layers is larger than a size of a surface of the base material facing the second reinforcing substrate.

In the method of manufacturing a radiation detector according to a twenty-first aspect of the present disclosure based on the method of manufacturing the radiation detector according to any one of the first to twenty-sixth aspects, a size of a surface of the base material facing the second reinforcing substrate is smaller than a size of a surface of the second reinforcing substrate facing the base material.

In the method of manufacturing a radiation detector of a twenty-second aspect of the present disclosure based on the method of manufacturing a radiation detector of any one of the first to twenty-ninth aspects, at least a part of an end part of the base material is located outside an end part of the second reinforcing substrate.

According to the present disclosure, it is possible to suppress that a defect occurs in the substrate, and the peeling property in the reworking process is excellent.

BRIEF DESCRIPTION OF THE DRAWINGS

Exemplary embodiments according to the technique of the present disclosure will be described in detail based on the following figures, wherein.

DETAILED DESCRIPTION

Figure 1:
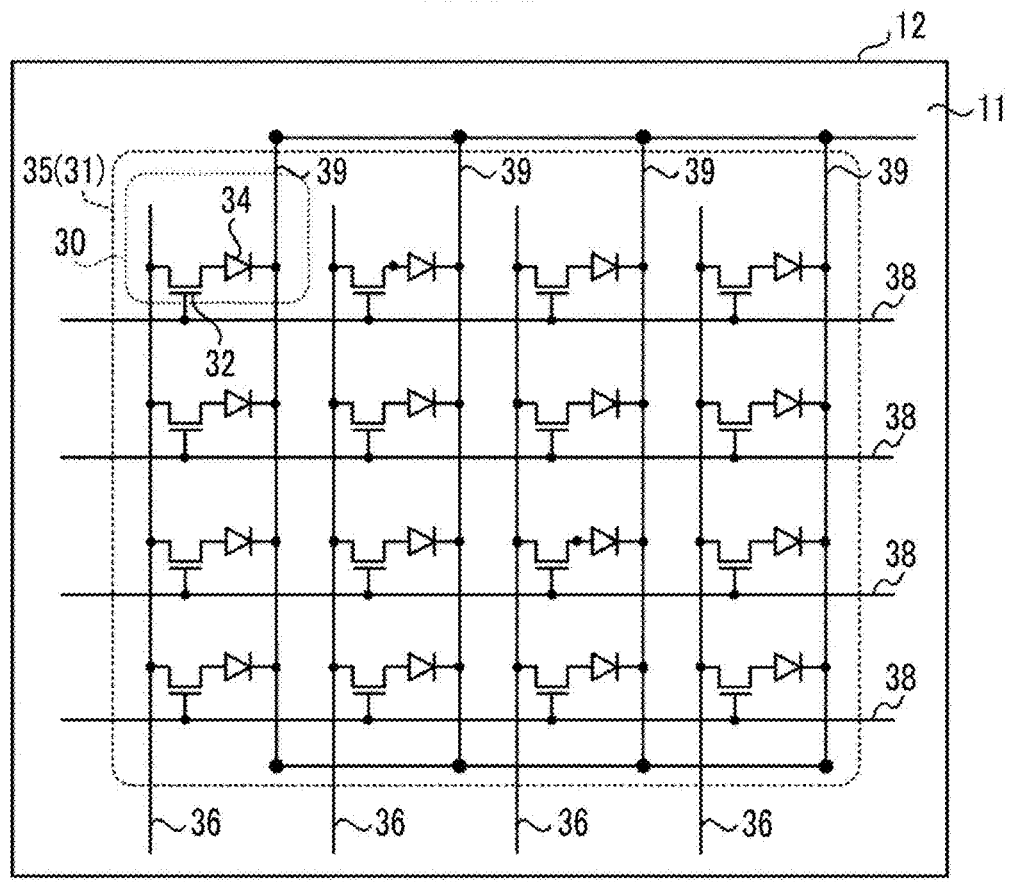
FIG. 1 is a configuration diagram illustrating an example of a configuration of a thin film transistor (TFT) substrate in a radiation detector according to an embodiment.

Hereinafter, embodiments of the present invention will be described in detail with reference to the drawings. In addition, the present embodiments do not limit the present invention.

A radiation detector of a radiographic imaging apparatus of the present embodiment has a function of detecting radiation transmitted through a subject to output image information representing a radiographic image of the subject. The radiation detector of the present embodiment comprises a thin film transistor (TFT) substrate, and a conversion layer that converts radiation into light (refer to a TFT substrate 12 and a conversion layer 14 of a radiation detector 10 in FIG. 3).

First, an example of the configuration of the TFT substrate 12 in the radiation detector of the present embodiment will be described with reference to FIG. 1. In addition, the TFT substrate 12 of the present embodiment is a substrate in which a pixel array 31 including a plurality of pixels 30 is formed in a pixel region 35 of a base material 11. Therefore, in the following description, the expression "the pixel region 35" is used as the same meaning as "the pixel array 31". The TFT substrate 12 of the present embodiment is an example of a substrate of the disclosed technique.

Each of the pixels 30 includes a sensor unit 34 and a switching element 32. The sensor unit 34 generates and accumulates electric charges in response to the light converted by the conversion layer. The switching element 32 reads out the electric charges accumulated in the sensor unit 34. In the present embodiment, as an example, a thin film transistor (TFT) is used as the switching element 32. For that reason, in the following description, the switching element 32 is referred to as a "TFT 32".

The plurality of pixels 30 are two-dimensionally disposed in one direction (a scanning wiring direction corresponding to a transverse direction of FIG. 1, hereinafter referred to as a "row direction"), and an intersection direction (a signal wiring direction corresponding to a longitudinal direction of FIG. 1, hereinafter referred as a "column direction") intersecting the row direction in the pixel region 35 of the TFT substrate 12. Although an array of the pixels 30 is illustrated in a simplified manner in FIG. 1, for example, 1024×1024 pixels 30 are disposed in the row direction and the column direction.

Additionally, a plurality of scanning wiring lines 38 for controlling switching states (ON and OFF) of the TFTs 32, and a plurality of signal wiring lines 36, which are provided for respective columns of the pixels 30 and from which electric charges accumulated in the sensor units 34 are read out, are provided in a mutually intersecting manner in the radiation detector 10. Each of the plurality of scanning wiring lines 38 is connected to a drive unit 103 (refer to FIG. 5) outside the radiation detector 10 via a flexible cable 112 (refer to FIGS. 3 and 5), and thereby, a control signal, which is output from the drive unit 103 to control the switching state of the TFT 32, flow to each scanning wiring line 38. Additionally, each of the plurality of signal wiring lines 36 is connected to a signal processing unit 104 (refer to FIG. 5) outside the radiation detector 10 via the flexible cable 112 (refer to FIGS. 3 and 5), and thereby, an electric charge read out from each pixel 30 is output to the signal processing unit 104.

Additionally, common wiring lines 39 are provided in a wiring direction of the signal wiring lines 36 at the sensor units 34 of the respective pixels 30 in order to apply bias voltages to the respective pixels 30. Bias voltages are applied to the respective pixels 30 from a bias power source by connecting the common wiring lines 39 to the bias power source outside the radiation detector 10 via terminals (not illustrated) provided in the TFT substrate 12.

Figure 2:
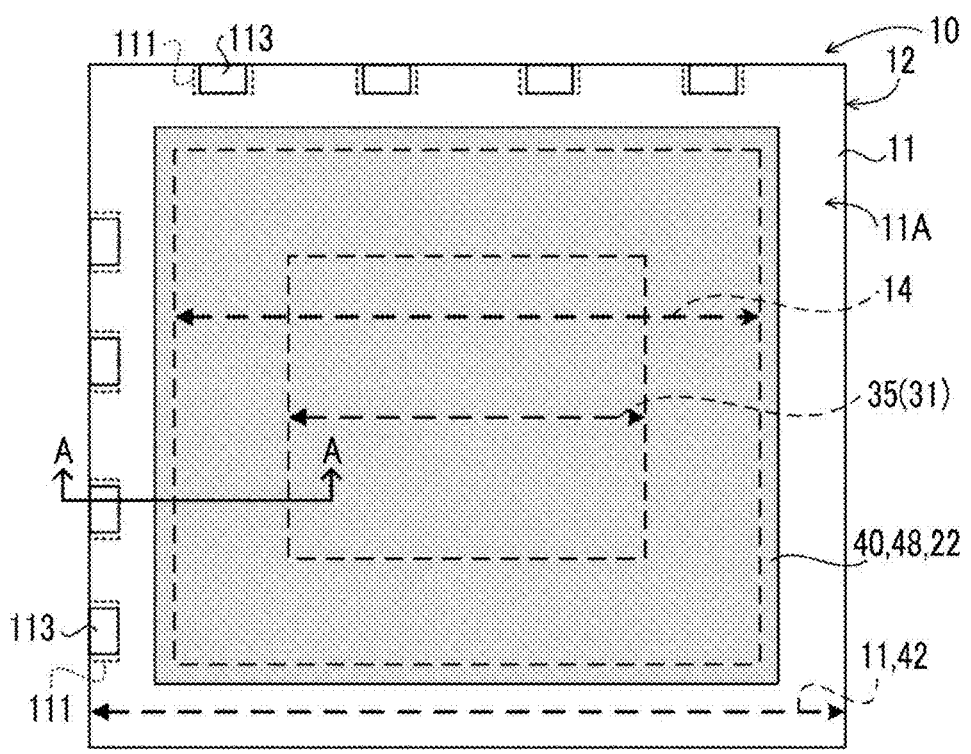
FIG. 2 is a plan view of an example of the radiation detector of the embodiment as seen from the side on which a conversion layer is provided.
Figure 3:
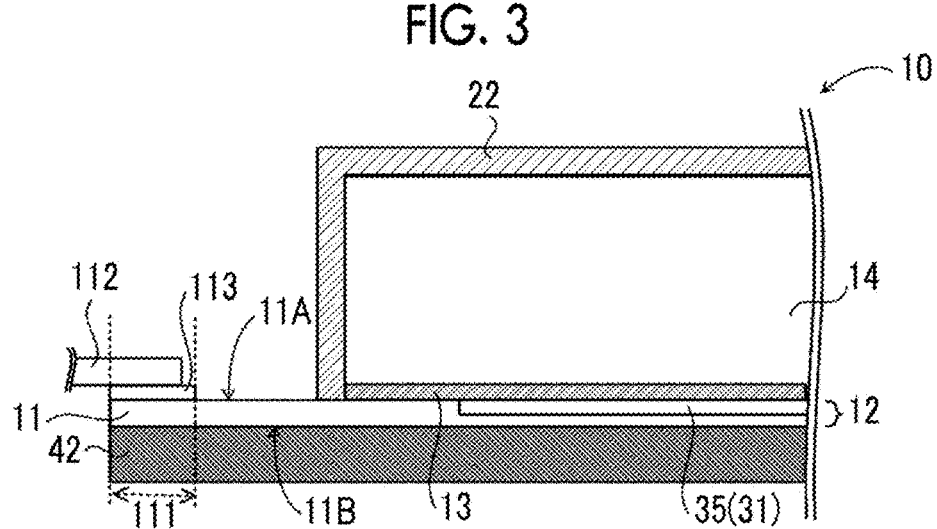
FIG. 3 is a cross-sectional view taken along line A-A of the radiation detector illustrated in FIG. 2.

Moreover, the radiation detector 10 of the present embodiment will be described in detail. FIG. 2 is an example of a plan view of the radiation detector 10 according to the present embodiment as seen from a first surface 11A side of the base material 11. Additionally, FIG. 3 is a cross-sectional view taken along line A-A of the radiation detector 10 in FIG. 2.

The first surface 11A of the base material 11 is provided with a pixel region 35 provided with the above-described pixels 30 and a terminal region 111.

The base material 11 is a resin sheet that has flexibility and includes, for example, a plastic such as a polyimide (PI). The thickness of the base material 11 may be a thickness such that desired flexibility is obtained in response to the hardness of a material, the size of the TFT substrate 12 (the area of the first surface 11A or a second surface 11B), and the like. In a case where a rectangular base material 11 is a single body, an example having flexibility indicates one in which the base material 11 hangs down (is lower than the height of a fixed side) 2 mm or more due to the gravity of the base material 11 resulting from its own weight at a position 10 cm away from the fixed side with one side of the base material 11 fixed. As a specific example in a case where the base material 11 is the resin sheet, the thickness thereof may be 5 µm to 125 µm, and the thickness thereof may be more preferably 20 µm to 50 µm.

In addition, the base material 11 has characteristics capable of withstanding the manufacture of the pixels 30 and has characteristics capable of withstanding the manufacture of amorphous silicon TFT (a-Si TFT) in the present embodiment. As such characteristics of the base material 11, it is preferable that the coefficient of thermal expansion (CTE) at 300° C. to 400° C. is about the same as the coefficient of thermal expansion of amorphous silicon (a-Si) wafer (for example, ±5 ppm/K). Specifically, the coefficient of thermal expansion of the base material 11 at 30° C. to 400° C. is preferably 20 ppm/K or less. Additionally, as the heat shrinkage percentage of the base material 11, it is preferable that the heat shrinkage percentage at 400° C. is 0.5% or less with the thickness being 25 μm. Additionally, it is preferable that the modulus of elasticity of the base material 11 does not have a transition point that general PI has, in a temperature range of 300° C. to 400° C., and the modulus of elasticity at 500° C. is 1 GPa or more.

Figure 4A:
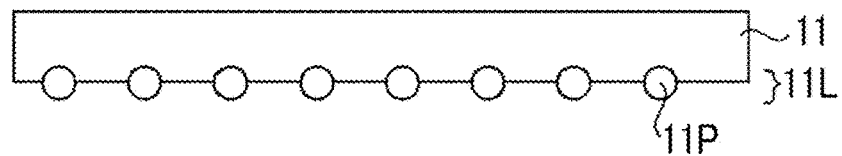
FIG. 4A is a cross-sectional view for explaining an example of a base material.
Figure 4B:
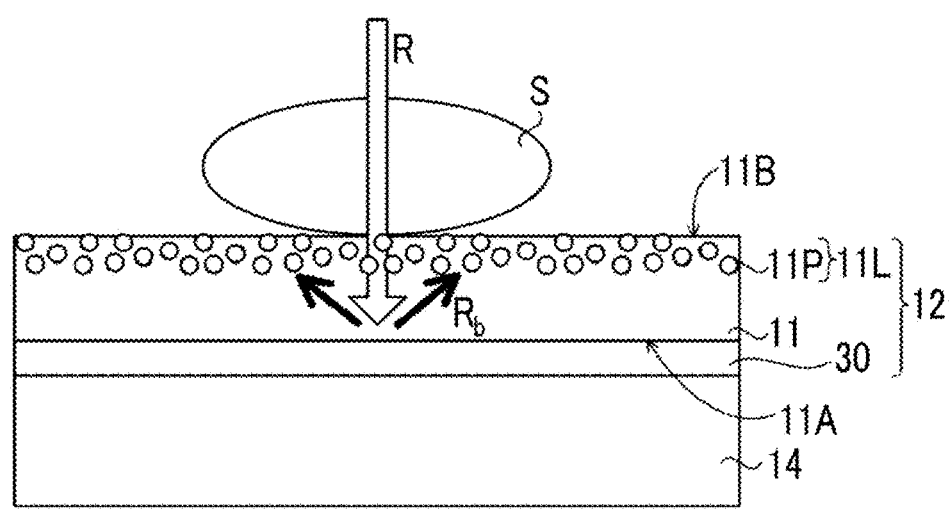
FIG. 4B is an explanatory view for explaining backscattered rays generated in the base material having a fine particle layer due to radiation transmitted through a subject.

Additionally, as illustrated in FIGS. 4A and 4B, it is preferable that the base material 11 of the present embodiment has a fine particle layer 11L containing inorganic fine particles 11P of which the average particle diameter is 0.05 μm or more and 2.5 μm or less. In addition, FIG. 4B illustrates an example in a case where the radiation detector 10 of the present embodiment is applied to an irradiation side sampling (ISS) type radiation detector in which radiation R is radiated from the TFT substrate 12 side.

Figure 4C:
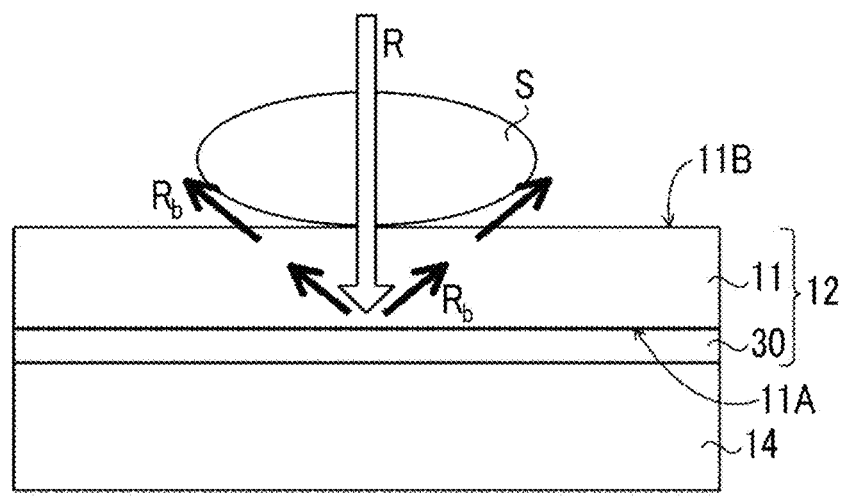
FIG. 4C is an explanatory view for explaining backscattered rays generated in the base material having no fine particle layer due to the radiation transmitted through the subject.

As illustrated in FIGS. 4B and 4C, in the base material 11, backscattered rays Rb are generated by the radiation R transmitted through a subject S. In a case where the base material 11 is made of a resin such as PI, the base material 11 is an organic substance. Therefore, the backscattered rays Rb of atoms such as C, H, O, and N constituting the organic substance and having relatively small atomic numbers increase due to the Compton effect.

As illustrated in FIG. 4B, in a case where the base material 11 has the fine particle layer 11L containing the fine particles 11P that absorb the backscattered rays Rb generated in the base material 11, compared to a case where the base material 11 does not have the fine particle layer 11L (refer to FIG. 4C), the backscattered rays Rb, which are transmitted through the base material 11 and scattered backward, are suppressed, which is preferable.

As such fine particles 11P, an inorganic substance including atoms, which has a small amount of the backscattered rays Rb generated by itself and absorb the backscattered rays Rb while absorbing less radiation R transmitted through the subject S, is preferable. In addition, there is a trade-off relationship between the suppression of the backscattered rays Rb and the transmissivity of the radiation R. From the viewpoint of suppressing backscattered rays Rb, it is preferable that the fine particles 11P contain elements having an atomic number larger than C, H, O, N, and the like constituting the resin of the base material 11. On the other hand, the larger the atomic number, the higher the ability to absorb the backscattered rays Rb. However, in a case where the atomic number exceeds 30, the amount of the radiation R absorbed increases and the dose of the radiation R reaching the conversion layer 14 decreases remarkably, which is not preferable. For that reason, as the fine particles 11P, in the case of a resinous base material 11, it is preferable to use an inorganic substance of which the atomic number is larger than the atoms constituting the organic substance that is the base material 11 and the atomic number is 30 or less. Specific examples of such fine particles 11P include $SiO_2$ that is an oxide of Si having an atomic number of 14, MgO that is an oxide of Mg having an atomic number of 12, $Al_2O_3$ that is an oxide of Al having an atomic number of 13, $TiO_2$ that is an oxide of Ti having an atomic number of 22, and the like.

A specific example of the resin sheet having such characteristics is XENOMAX (registered trademark).

In addition, the above thicknesses in the present embodiment were measured using a micrometer. The coefficient of thermal expansion was measured according to JIS K7197: 1991. In addition, the measurement was performed by cutting out test pieces from a main surface of the base material 11 while changing the angle by 15 degrees, measuring the coefficient of thermal expansion of each of the cut-out test pieces, and setting the highest value as the coefficient of thermal expansion of the base material 11. The coefficient of thermal expansion is measured at intervals of 10° C. between −50° C. and 450° C. in a machine direction (MD) and a transverse direction (TD), and (ppm/° C.) is converted to (ppm/K). For the measurement of the coefficient of thermal expansion, the TMA4000S apparatus made by MAC Science Co., Ltd. is used, sample length is 10 mm, sample width is 2 mm, initial load is 34.5 $g/mm^2$, temperature rising rate is 5° C./min, and the atmosphere is in argon. The modulus of elasticity was measured according to JIS K7171:2016. In addition, the measurement was performed by cutting out test pieces from the main surface of the base material 11 while changing the angle by 15 degrees, performing a tensile test for each of the cut-out test pieces, and setting the highest value as the modulus of elasticity of the base material 11.

In addition, there is a case where irregularities may occur on the surface of the base material 11 due to the fine particles 11P contained in the fine particle layer 11L. There is a case where it is difficult to form the pixels 30 in a state in which the irregularities have occurred on the surface of the base material 11 in this way. For that reason, as illustrated in FIG. 4B, it is preferable that the base material 11 has the fine particle layer 11L on the second surface 11B opposite to the first surface 11A on which the pixels 30 are formed. In other words, the base material 11 preferably has the fine particle layer 11L on the second surface 11B opposite to the first surface 11A on which the conversion layer 14 is provided.

Additionally, in order to sufficiently absorb the backscattered rays Rb generated in the base material 11, it is preferable to have the fine particle layer 11L on the surface of the base material 11 close to the subject S. As illustrated in FIG. 4B, in the ISS type radiation detector 10, it is preferable to have the fine particle layer 11L on the second surface 11B.

In this way, in the ISS type radiation detector 10, the base material 11 has the fine particle layer 11L on the second surface 11B, so that the pixels 30 can be accurately formed and the backscattered rays Rb can be effectively suppressed.

In addition, the base material 11 having desired flexibility is not limited to resinous materials such as the resin sheet. For example, the base material 11 may be a glass substrate or the like having a relatively small thickness. As a specific example of a case where the base material 11 is the glass substrate, generally, in a size of about 43 cm on a side, the glass substrate has flexibility as long as the thickness is 0.3 mm or less. Therefore, any desired glass substrate may be used as long as the thickness is 0.3 mm or less.

As illustrated in FIGS. 2 and 3, the conversion layer 14 is provided on the pixel region 35 of the present embodiment. The conversion layer 14 is provided on a partial region of the first surface 11A of the base material 11 including the pixel region 35. In this way, the conversion layer 14 of the present embodiment is not provided on the region of an outer peripheral part on the first surface 11A of the base material 11. In addition, here, the term "on" in the structure of the radiation detector 10 means "on" in a positional relationship with reference to the TFT substrate 12 side. For example, the conversion layer 14 is provided on the TFT substrate 12.

In the present embodiment, a scintillator including CsI (cesium iodide) is used as an example of the conversion layer 14. It is preferable that such a scintillator includes, for example, CsI:Tl (cesium iodide to which thallium is added) or CsI:Na (cesium iodide to which sodium is added) having an emission spectrum of 400 nm to 700 nm at the time of X-ray radiation. In addition, the emission peak wavelength in a visible light region of CsI:Tl is 565 nm.

In the radiation detector 10 of the present embodiment, the conversion layer 14 is directly formed on the TFT substrate 12 as strip-shaped columnar crystals (not illustrated) by vapor-phase deposition methods, such as a vacuum vapor deposition method, a sputtering method, and a chemical vapor deposition (CVD) method. For example, in a case where CsI:Tl is used as the conversion layer 14, a vacuum vapor deposition method is used as a method of forming the conversion layer 14. In the vacuum vapor deposition method, CsI:Tl is heated and gasified by heating means, such as a resistance heating-type crucible in an environment with a vacuum degree of 0.01 Pa to 10 Pa, and CsI:Tl is deposited on the TFT substrate 12 with the temperature of the TFT substrate 12 as the room temperature (20° C.) to 300° C. As the thickness of the conversion layer 14, 100 μm to 800 μm is preferable.

In the present embodiment, as illustrated in FIG. 3 as an example, a buffer layer 13 is provided between the TFT substrate 12 and the conversion layer 14. The buffer layer 13 has a function of buffering a difference between the coefficient of thermal expansion of the conversion layer 14 and the coefficient of thermal expansion of the base material 11. In addition, unlike the radiation detector 10 of the present embodiment, a configuration may be adopted in which the buffer layer 13 is not provided. However, as the difference between the coefficient of thermal expansion of the conversion layer 14 and the coefficient of thermal expansion of the base material 11 is larger, it is preferable to provide the buffer layer 13. For example, in a case where the above XENOMAX (registered trademark) is used for the base material 11, the difference from the coefficient of thermal expansion of the conversion layer 14 is larger than the coefficient of thermal expansion of other materials. Therefore, it is preferable to provide the buffer layer 13 as in the radiation detector 10 illustrated in FIG. 3. As the buffer layer 13, a PI membrane or a parylene (registered trademark) membrane is used.

The protective layer 22 has a function of protecting the conversion layer 14 from moisture, such as humidity. Examples of the material of the protective layer 22 include organic films, and specifically single films or laminated films made of polyethylene terephthalate (PET), polyphenylene sulfide (PPS), biaxially oriented polypropylene film (OPP), polyethylene naphthalate (PEN), PI, and the like. Additionally, as the protective layer 22, a laminated film of a resin film and a metal film may be used. Examples of the laminated film of the resin film and the metal film include an Alpet (registered trademark) sheet in which aluminum is laminated by causing an aluminum foil to adhere to an insulating sheet (film) such as PET.

A second reinforcing substrate 42 is provided on the entire second surface 11B of the base material 11. In addition, a pressure sensitive adhesive layer for providing the second reinforcing substrate 42, a protective film having a moistureproof function, or the like may be provided between the second surface 11B of the base material 11 and the second reinforcing substrate 42.

The second reinforcing substrate 42 has a higher bending stiffness than the base material 11, and a dimensional change (deformation) due to a force applied in a direction perpendicular to the surface facing the conversion layer 14 is smaller than a dimensional change due to a force applied in a direction perpendicular to the second surface 11B of the base material 11. Specifically, the bending stiffness of the second reinforcing substrate 42 is preferably 100 times or more the bending stiffness of the base material 11. Additionally, the thickness of the second reinforcing substrate 42 of the present embodiment is larger than the thickness of the base material 11. For example, in a case where XENOMAX (registered trademark) is used as the base material 11, the thickness of the second reinforcing substrate 42 is preferably about 0.2 mm to 0.25 mm. In addition, the bending stiffness referred to here means the difficulty of bending and that the higher the bending stiffness, the more difficult it is to bend.

Specifically, a material having a bending modulus of elasticity of 150 MPa or more and 2,500 MPa or less is preferably used for the second reinforcing substrate 42 of the present embodiment. A method of measuring the bending modulus of elasticity is based on, for example, JIS K 7171:2016 Standard. From the viewpoint of suppressing the deflection of the base material 11, the second reinforcing substrate 42 preferably has a higher bending stiffness than the base material 11. In addition, in a case where the bending modulus of elasticity is low, the bending stiffness is also low. In order to obtain a desired bending stiffness, the thickness of the second reinforcing substrate 42 should be made large, and the thickness of the entire radiation detector 10 increases. Considering the above-described material of the second reinforcing substrate 42, the thickness of the second reinforcing substrate 42 tends to be relatively large in a case where a bending stiffness exceeding 140,000 Pacm$^4$ is to be obtained. For that reason, in view of obtaining appropriate stiffness and considering the thickness of the entire radiation detector 10, the material used for the second reinforcing substrate 42 preferably has a bending modulus of elasticity of 150 MPa or more and 2,500 MPa or less. Additionally, the bending stiffness of the second reinforcing substrate 42 is preferably 540 Pacm$^4$ or more and 140,000 Pacm$^4$ or less.

Additionally, it is preferable that the coefficient of thermal expansion of the second reinforcing substrate 42 of the present embodiment is closer to the coefficient of thermal expansion of the material of the conversion layer 14. The ratio of the coefficient of thermal expansion of the second reinforcing substrate 42 to the coefficient of thermal expansion of the conversion layer 14 (the coefficient of thermal expansion of the second reinforcing substrate 42/the coefficient of thermal expansion of the conversion layer 14) is preferably 0.5 or more and 2 or less. The coefficient of thermal expansion of such a second reinforcing substrate 42 is preferably 30 ppm/K or more and 80 ppm/K or less. For example, in a case where the conversion layer 14 has CsI:Tl as a material, the coefficient of thermal expansion of the conversion layer 14 is 50 ppm/K. In this case, examples of materials relatively close to the conversion layer 14 include polyvinyl chloride (PVC) having a coefficient of thermal expansion of 60 ppm/K to 80 ppm/K, acrylic having a coefficient of thermal expansion of 70 ppm/K to 80 ppm/K, PET having a coefficient of thermal expansion of 65 ppm/K to 70 ppm/K, polycarbonate (PC) having a coefficient of thermal expansion of 65 ppm/K, Teflon (registered trademark) having a coefficient of thermal expansion of 45 ppm/K to 70 ppm/K, and the like.

Moreover, considering the above-described bending modulus of elasticity, the material of the second reinforcing substrate 42 is more preferably a material containing at least one of PET or PC.

From the viewpoint of elasticity, the second reinforcing substrate 42 preferably contains a material having a yield point. In addition, in the present embodiment, the "yield point" means a phenomenon in which the stress rapidly decreases once in a case where the material is pulled, means that the strain is increased without increasing the stress on a curve representing a relationship between the stress and the strain, and indicates the peak of a stress-strain curve in a case where a tensile strength test is performed on the material. Resins having the yield point generally include resins that are hard and strongly sticky, and resins that are soft and strongly sticky and have medium strength. Examples of the hard and strongly sticky resins include PC and the like. Additionally, examples of the resins that are soft and strongly sticky and have medium strength include polypropylene and the like.

The second reinforcing substrate 42 of the present embodiment is a substrate having plastic as a material. In a case where the plastic used as the material for the second reinforcing substrate 42 is preferably a thermoplastic resin for the above-described reasons, and include at least one of PC, PET, styrol, acrylic, polyacetase, nylon, polypropylene, acrylonitrile butadiene styrene (ABS), engineering plastics, or polyphenylene ether. In addition, the second reinforcing substrate 42 is preferably at least one of polypropylene, ABS, engineering plastics, PET, or polyphenylene ether among these, is more preferably at least one of styrol, acrylics, polyacetase, or nylon, and is even more preferably at least one of PC or PET.

Additionally, as illustrated in FIGS. 2 and 3, the terminal region 111 of the base material 11 is provided with a terminal 113 to which the flexible cable 112 is connected. The terminal region 111 in the present embodiment includes at least a region where the terminal 113 is provided, and the area of the terminal region 111 is equal to or larger than the area of the terminal 113. The range of the terminal region 111 is determined depending on the ease of reworking the flexible cable 112. Specifically, the range (area) of the terminal region 111 is determined in response to the respective areas of the flexible cable 112 and the terminal 113, the connection deviation between the flexible cable 112 and the terminal 113 in a case where the flexible cable 112 is reworked, the method of the reworking, and the like. In addition, removing a cable or component connected to the base material 11 (TFT substrate 12) to reconnect a new cable or component due to a defect or a positional deviation is referred to as the reworking. For example, an anisotropic conductive film or the like is used for the terminal 113.

In addition, in the following description, in a case where the flexible cable 112 is connected to the terminal 113 of the terminal region 111, the flexible cable 112 is simply connected to the terminal region 111. Additionally, in the present embodiment, the connection related to a component referred to as a "cable" including the flexible cable 112 means an electrical connection unless otherwise specified. In addition, the flexible cable 112 includes a signal line (not illustrated) made of a conductor, and the signal line is connected to the terminal 113, and thereby electrically connected thereto. In the following, the term "cable" refers to a flexible cable (having flexibility).

Figure 5:
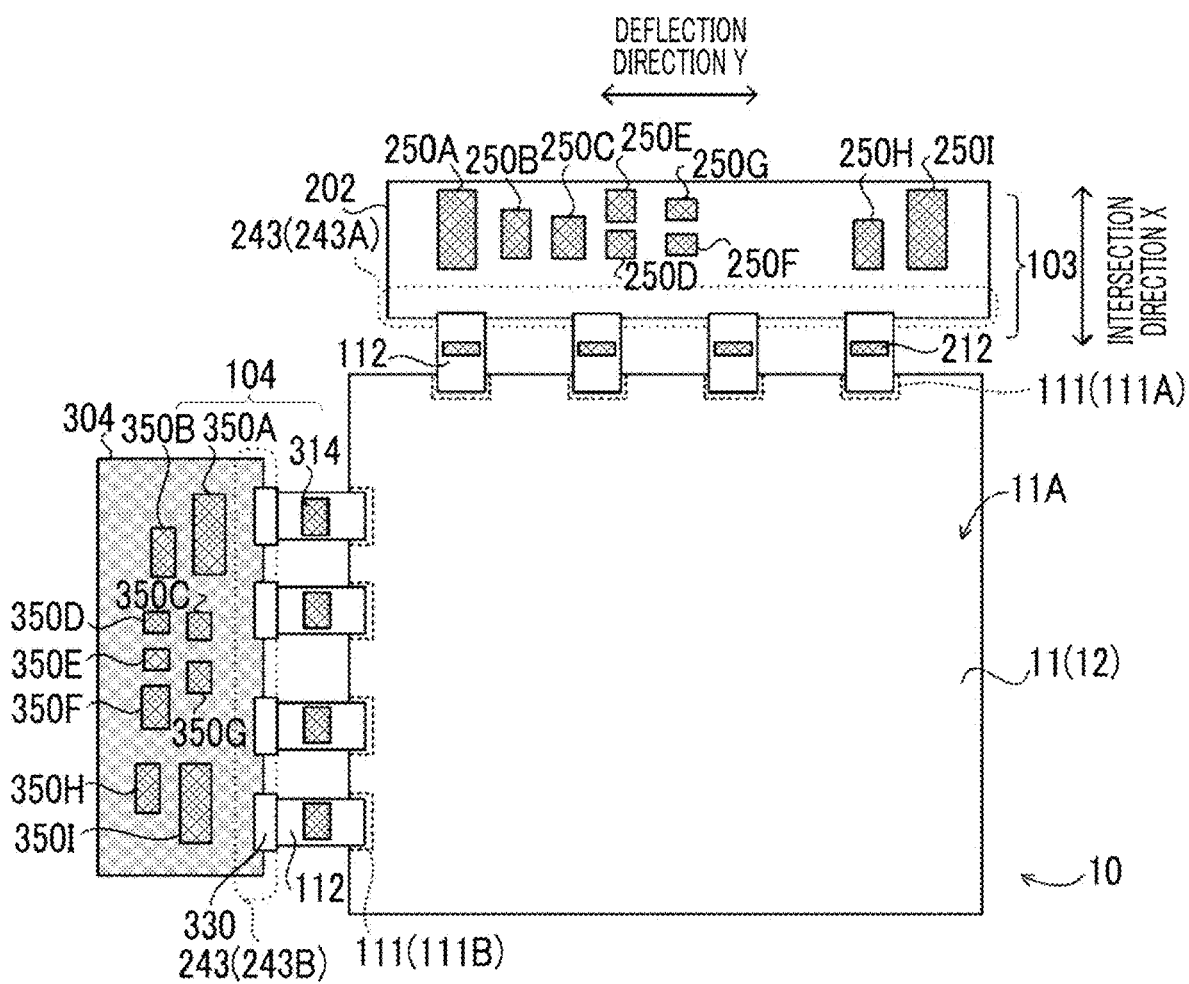
FIG. 5 is a plan view of the example of the radiation detector of the embodiment as seen from a first surface side of a TFT substrate.

As described above, the flexible cable 112 is connected to at least one of the drive unit 103 or the signal processing unit 104 (refer to FIG. 5 for both). FIG. 5 illustrates a plan view of an example of a state in which the drive unit 103 and the signal processing unit 104 are connected to the radiation detector 10 of the present embodiment by the flexible cable 112 as seen from the first surface 11A side of the base material 11. The drive unit 103 and the signal processing unit 104 of the present embodiment are examples of a circuit unit of the present disclosure.

As in the example illustrated in FIG. 5, one end of each of a plurality of (four in FIG. 5) the flexible cables 112 is thermocompression-bonded to the terminal 113 (not illustrated in FIG. 5) in the terminal region 111 (111A). The flexible cable 112 has a function of connecting the drive unit 103 and the scanning wiring lines 38 (refer to FIG. 1). A plurality of signal lines (not illustrated) included in the flexible cable 112 are connected to the scanning wiring lines 38 (refer to FIG. 1) of the TFT substrate 12 via the terminal region 111 (111A).

On the other hand, the other end of the flexible cable 112 is thermocompression-bonded to a connection region 243 (243A) provided in an outer peripheral region of a driving substrate 202. The plurality of signal lines (not illustrated) included in the flexible cable 112 are connected to drive components 250 that are a circuit, an element, and the like mounted on the driving substrate 202 via the connection region 243.

FIG. 5 illustrates, as an example, a state in which nine drive components 250 (250A to 250I) are mounted on the driving substrate 202. As illustrated in FIG. 5, the drive components 250 of the present embodiment are disposed in an intersection direction X that is a direction intersecting a deflection direction Y that is a direction along a side corresponding to the terminal region 111 (111A) of the base material 11. For example, in a case where the drive components 250 each have a long side and a short side, the drive components 250 are disposed in a state in which the long side extends in the intersection direction X.

The driving substrate 202 of the present embodiment is a flexible printed circuit board (PCB) substrate, which is a so-called flexible substrate. The drive components 250 mounted on the driving substrate 202 is a component mainly used for processing digital signals (hereinafter, referred to as "digital components"). Specific examples of the drive components 250 include a digital buffer, a bypass capacitor, a pull-up/pull-down resistor, a damping resistor, an electro magnetic compatibility (EMC) countermeasure chip component, and the like. In addition, the driving substrate 202 may not necessarily be a flexible substrate, and may be a non-flexible rigid substrate, which will be described below.

Digital components tend to have a relatively smaller area (size) than analog components to be described below. Additionally, the digital components tend to be less susceptible to electrical interference, in other words, noise than the analog components. For that reason, in the present embodiment, in a case where the TFT substrate 12 is deflected, the side of a substrate that is deflected with the deflection of the TFT substrate 12 is the driving substrate 202 on which the drive components 250 are mounted.

Additionally, a drive circuit unit 212 is mounted on the flexible cable 112 connected to the driving substrate 202. The drive circuit unit 212 is connected to the plurality of signal lines (not illustrated) included in the flexible cable 112.

In the present embodiment, the drive unit 103 is realized by the drive components 250 mounted on the driving substrate 202, and the drive circuit unit 212. The drive circuit unit 212 is an integrated circuit (IC) including a circuit different from the drive components 250 mounted on the driving substrate 202 among various circuits and elements that realize the drive unit 103.

In this way, in the radiation detector 10 of the present embodiment, the TFT substrate 12 and the driving substrate 202 are electrically connected to each other by the flexible cable 112, and thereby, the drive unit 103 and each of the scanning wiring lines 38 are connected to each other.

Meanwhile, one end of each of the plurality of (four in FIG. 5) flexible cables 112 is thermocompression-bonded to the terminal region 111 (111B) of the base material 11. The plurality of signal lines (not illustrated) included in the flexible cable 112 are connected to the signal wiring lines 36 (refer to FIG. 1) via the terminal region 111 (111B). The flexible cable 112 has a function of connecting the signal processing unit 104 and the signal wiring lines 36 (refer to FIG. 1) to each other.

Meanwhile, the other end part of the flexible cable 112 is electrically connected to a connector 330 provided in the connection region 243 (243B) of a signal processing substrate 304. The plurality of signal lines (not illustrated) included in the flexible cable 112 are connected to signal processing components 350 that are a circuit, an element, and the like mounted on the signal processing substrate 304 via the connector 330. For example, examples of the connector 330 include a zero insertion force (ZIF) structure connector and a Non-ZIF structure connector. FIG. 5 illustrates, as an example, a state in which nine signal processing components 350 (350A to 350I) are mounted on the signal processing substrate 304. As illustrated in FIG. 5, the signal processing components 350 of the present embodiment are disposed in the intersection direction X that is a direction along a side of the base material 11 provided with the terminal region 111 (111B) of the base material 11. For example, in a case where the signal processing components 350 each have a long side and a short side, the signal processing components 350 are disposed in a state in which the long side extends in the intersection direction X.

In addition, the signal processing substrate 304 of the present embodiment may not necessarily be a flexible substrate, and may be a non-flexible PCB substrate or a so-called rigid substrate. In a case where the rigid substrate is used as the signal processing substrate 304, the thickness of the signal processing substrate 304 is larger than the thickness of the driving substrate 202. Additionally, the stiffness of the signal processing substrate 304 is higher than that of the driving substrate 202.

The signal processing components 350 mounted on the signal processing substrate 304 are components mainly used for processing analog signals (hereinafter, referred to as "analog components"). Specific examples of the signal processing components 350 include an operational amplifier, an analog-to-digital converter (ADC), a digital-to-analog converter (DAC), a power supply IC, and the like. Additionally, the signal processing components 350 of the present embodiment also include a coil around a power supply having a relatively large component size, and a large-capacity smoothing capacitor.

As described above, the analog components tend to have a relatively larger area (size) than the digital components. Additionally, the analog components tend to be more susceptible to electrical interference, in other words, noise, than the digital components. For that reason, in the present embodiment, even in a case where the TFT substrate 12 is deflected, the side of the substrate that is not deflected (is not affected by the deflection) is the signal processing substrate 304 on which the signal processing components 350 are mounted.

Additionally, a signal processing circuit unit 314 is mounted on the flexible cable 112 connected to the signal processing substrate 304. The signal processing circuit unit 314 is connected to a plurality of signal lines (not illustrated) included in the flexible cable 112B.

In the present embodiment, the signal processing unit 104 is realized by the signal processing components 350 mounted on the signal processing substrate 304, and the signal processing circuit unit 314. The signal processing circuit unit 314 is an IC including a circuit different from the signal processing components 350 mounted on the signal processing substrate 304 among various circuits and elements that realize the signal processing unit 104.

In this way, in the radiation detector 10 of the present embodiment, the TFT substrate 12 and the signal processing substrate 304 are electrically connected to each other by the flexible cable 112, and thereby the signal processing unit 104 and each of the signal wiring lines 36 are connected to each other.

Next, an example of the method of manufacturing the radiation detector 10 of the present embodiment will be described with reference to FIGS. 6A to 6H.

In advance, one in which the adhesive layer 48 is applied to the first reinforcing substrate 40 having a desired size adapted to the radiation detector 10 is prepared. The adhesive layer 48 is a layer made of an adhesive, which allows the first reinforcing substrate 40 to adhere to the TFT substrate 12 in a first reinforcing substrate disposing step (refer to FIGS. 6D and 6E), which will be described in detail below and allows the first reinforcing substrate 40 to be peeled from the TFT substrate 12 in a first reinforcing substrate peeling step (refer to FIG. 6H), which will be described in detail below. Examples of this type of adhesive include dismantleable adhesives. The type of the dismantleable adhesives, specifically, the method of losing the adhesiveness of the dismantleable adhesives depends on the method of peeling the first reinforcing substrate 40 in the first reinforcing substrate peeling step (refer to FIG. 6H).

Figure 6A:
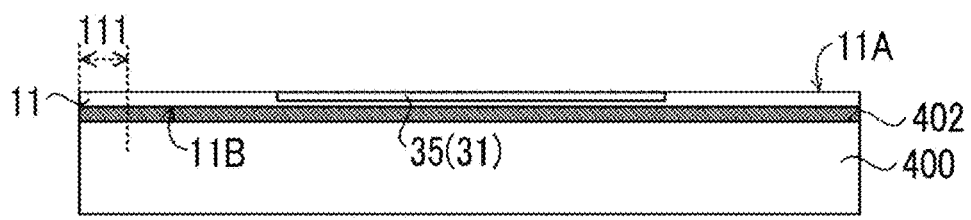
FIG. 6A is a view illustrating an example of a TFT substrate forming step in an example of a method of manufacturing a radiation detector according to the embodiment.

First, the TFT substrate 12 is formed by a substrate forming step illustrated in FIG. 6A. In the present embodiment, as an example, the base material 11 is formed on a support body 400, such as a glass substrate which is thicker than the base material 11, via a peeling layer 402. In a case where the base material 11 is formed by a lamination method, a sheet to be the base material 11 is bonded onto the support body 400. The surface of the base material 11 corresponding to the second surface 11B is the support body 400 side and is in contact with the peeling layer 402.

Moreover, the plurality of pixels 30 are formed in the pixel region 35 of the base material 11. In addition, in the present embodiment, as an example, the plurality of pixels 30 are formed on the pixel region 35 of the base material 11 via an undercoat layer (not illustrated) made of SiN or the like.

Figure 6B:
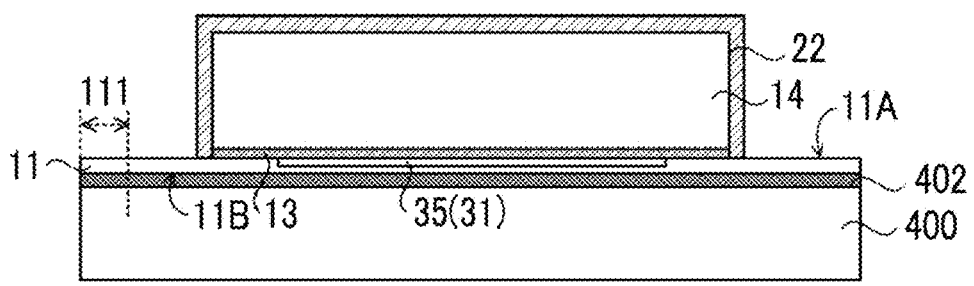
FIG. 6B is a view illustrating an example of a conversion layer substrate forming step in the example of the method of manufacturing a radiation detector according to the embodiment.

Next, the conversion layer 14 is formed on the pixel region 35 by a conversion layer forming step illustrated in FIG. 6B. As an example, in the present embodiment, first, the buffer layer 13 is formed in a region where the conversion layer 14 is provided, on the first surface 11A of the base material 11. Thereafter, the CsI conversion layer 14 is formed as a columnar crystal directly on the TFT substrate 12 and more specifically on the buffer layer 13 by vapor-phase deposition methods such as a vacuum vapor deposition method, a sputtering method, and a chemical vapor deposition (CVD) method. In this case, the side of the conversion layer 14 in contact with the pixels 30 is a growth-direction base point side of the columnar crystal.

In addition, in a case where the CsI conversion layer 14 is provided directly on the TFT substrate 12 by the vapor-phase deposition method in this way, for example, a reflective layer (not illustrated) having a function of reflecting the light converted in the conversion layer 14 may be provided on the surface of the conversion layer 14 opposite to the side in contact with the TFT substrate 12. The reflective layer may be provided directly on the conversion layer 14 or may be provided via an adhesion layer or the like. As a material of the reflective layer, it is preferable to use an organic material, and it is preferable to use, for example, at least one of white PET, $TiO_2$, $Al_2O_3$, foamed white PET, a polyester-based high-reflection sheet, specular reflection aluminum, or the like. Particularly, it is preferable to use the white PET as the material from a viewpoint of reflectance. In addition, the polyester-based high-reflection sheet is a sheet (film) having a multilayer structure in which a plurality of thin polyester sheets are laminated.

Additionally, in a case where a CsI scintillator is used as the conversion layer 14, the conversion layer 14 can be formed on the TFT substrate 12 by a method different from the method of the present embodiment. For example, the conversion layer 14 may be formed on the TFT substrate 12 by preparing one in which CsI is vapor-deposited on an aluminum plate or the like by a vapor-phase deposition method and bonding a side of the CsI, which is not in contact with the aluminum plate, and the pixels 30 of the TFT substrate 12 to each other with a pressure sensitive adhesive sheet or the like. In this case, it is preferable that one in which the entire conversion layer 14 also including the aluminum plate is covered with a protective film is bonded to the pixel regions 35 of the TFT substrate 12. In addition, in this case, the side of the pixel region 35 in contact with the conversion layer 14 is a distal end side in the growth direction of the columnar crystal.

Additionally, unlike the radiation detector 10 of the present embodiment, GOS ($Gd_2O_2S:Tb$)) or the like may be used as the conversion layer 14 instead of CsI. In this case, for example, the conversion layer 14 can be formed on the TFT substrate 12 by preparing one in which a sheet having GOS dispersed in a binder such as resin is bonded to a support body formed of white PET or the like with a pressure sensitive adhesive layer or the like, and bonding a side of the GOS on which the support body is not bonded, and the pixel region 35 of the TFT substrate 12 to each other with the pressure sensitive adhesive sheet or the like. In addition, the conversion efficiency from radiation to visible light is higher in a case where CsI is used for the conversion layer 14 than in a case where GOS is used.

Moreover, the protective layer 22 is provided by application or bonding to cover an upper surface (a surface opposite to a surface on the base material 11 side) and a side surface of the conversion layer 14.

Figure 6C:
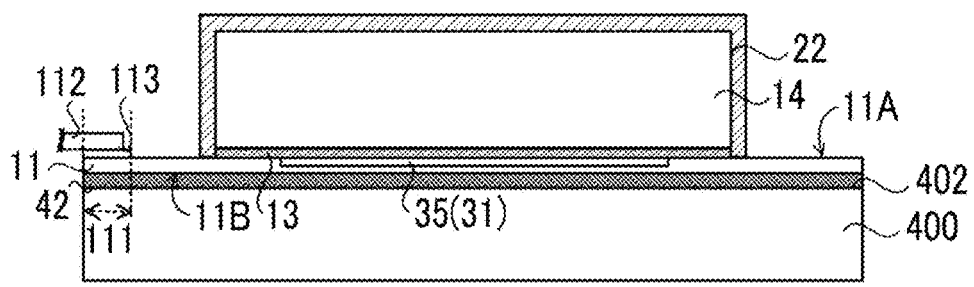
FIG. 6C is a view illustrating an example of a wiring connection forming step in the example of the method of manufacturing a radiation detector according to the embodiment.

Next, the flexible cable 112 is connected to the terminal 113 of the base material 11 by a wiring connection step illustrated in FIG. 6C. As an example, in the present embodiment, the flexible cable 112 is thermocompression-bonded to the terminal 113 of the terminal regions 111 of the base material 11, and the plurality of signal lines (not illustrated) included in the flexible cable 112 and the terminal region 111 of the base material 11 are electrically connected to each other.

Moreover, the flexible cable 112 is thermocompression-bonded to the connection region 243 (243A) of the driving substrate 202, and the plurality of signal lines (not illustrated) included in the flexible cable 112 and the drive components 250 mounted on the driving substrate 202 are electrically connected to each other and brought into a state illustrated in FIG. 5.

Figure 6D:
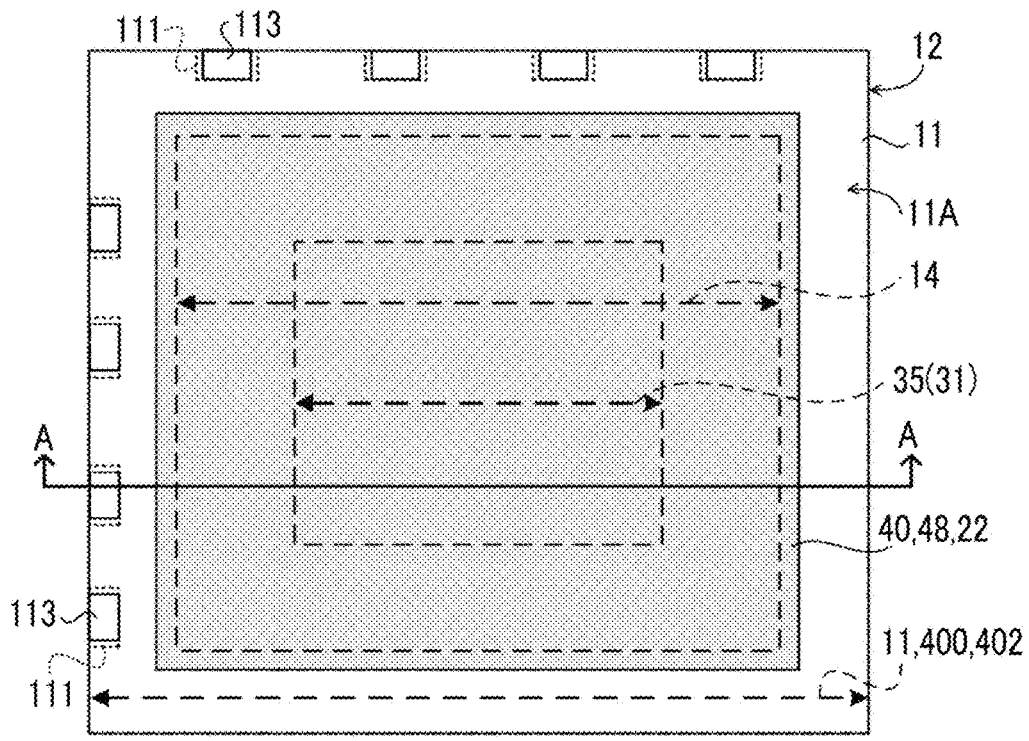
FIG. 6D is a view illustrating an example of a first reinforcing substrate disposing step in the example of the method of manufacturing a radiation detector according to the embodiment.
Figure 6E:
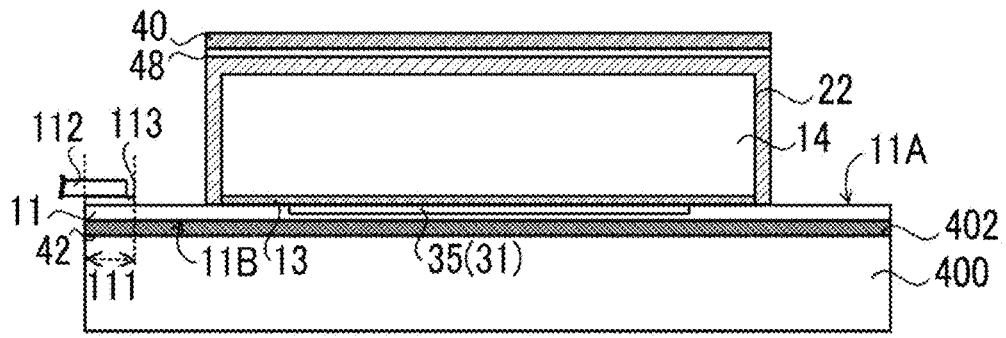
FIG. 6E is a cross-sectional view taken along line A-A of the radiation detector illustrated in FIG. 6D.

Next, the first reinforcing substrate 40 is provided on the conversion layer 14 by the first reinforcing substrate disposing step illustrated in FIGS. 6D and 6E. In addition, FIG. 6D is an example of a plan view of the radiation detector 10 in this step as seen from a first surface 11A side of the base material 11. Additionally, FIG. 6E is a cross-sectional view taken along line A-A of the radiation detector 10 in FIG. 6D.

As illustrated in FIGS. 6D and 6E, in the present embodiment, by performing the first reinforcing substrate disposing step, the first reinforcing substrate 40 is provided on the surface of the conversion layer 14, which is covered with the protective layer 22 and located opposite to the surface on the TFT substrate 12 side, more specifically, on the protective layer 22 by the adhesive layer 48.

As an example, in the present embodiment, the first reinforcing substrate 40, which has been prepared in advance, is bonded to the TFT substrate 12 on which the conversion layer 14 is formed and the flexible cable 112 is connected. The conversion layer 14 is sealed by the first reinforcing substrate 40. In addition, in a case where the above bonding is performed, the bonding is performed under the atmospheric pressure or under reduced pressure (under vacuum). However, in order to suppress entry of air or the like while being bonded to each other, it is preferable to perform the bonding under reduced pressure.

The first reinforcing substrate 40 has a function of suppressing a defect of the TFT substrate 12 that occurs in a case where the TFT substrate 12, more specifically, a laminate of the TFT substrate 12 and the conversion layer 14 is deflected in a support body peeling step (refer to FIG. 6F, will be described in detail below) performed after this step. In a case where the TFT substrate 12 is largely deflected, there is a concern that a defect may occur in the TFT substrate 12. For example, there is a concern that the conversion layer 14 may be peeled from the TFT substrate 12, and particularly, an end part of the conversion layer 14 may be easily peeled from the TFT substrate 12. Additionally, for example, as a result of the TFT substrate 12 being deflected, there is a concern that the pixels 30 may be damaged.

Thus, in the present embodiment, the first reinforcing substrate disposing step of providing the first reinforcing substrate 40 on the TFT substrate 12 to suppress that the TFT substrate 12 is largely deflected and suppress that a defect occurs in the TFT substrate 12 even in a case where the TFT substrate 12 is deflected is performed before the support body peeling step.

Similar to the second reinforcing substrate 42, the first reinforcing substrate 40 has a higher stiffness than the base material 11, and a dimensional change (deformation) due to a force applied in a direction perpendicular to a surface facing the first surface 11A is smaller than a dimensional change due to the force applied in a direction perpendicular to the first surface 11A in the base material 11. Additionally, the thickness of the first reinforcing substrate 40 of the present embodiment is larger than the thickness of the base material 11 and smaller than the thickness of the second reinforcing substrate 42. For example, in a case where XENOMAX (registered trademark) is used as the base material 11 and in a case where the thickness of the second reinforcing substrate 42 is about 0.2 mm to 0.25 mm as described above, the thickness of the first reinforcing substrate 40 is preferably about 0.1 mm.

Additionally, in the present embodiment, the bending stiffness of the first reinforcing substrate 40 is smaller than the bending stiffness of the second reinforcing substrate 42. In the present embodiment, the first reinforcing substrate 40 is deflected in a case where the TFT substrate 12 is peeled from the support body 400 in the support body peeling step (refer to FIG. 6F), which will be described in detail below, and in a case where the first reinforcing substrate 40 is peeled from the TFT substrate 12 in the first reinforcing substrate peeling step (refer to FIG. 6H), which will be described in detail below. For that reason, the first reinforcing substrate 40 of the present embodiment is likely to be deflected to the extent that the above peeling is possible, while having a bending stiffness of a height capable of suppressing that the TFT substrate 12 is largely deflected in order to suppress that a defect occurs in the TFT substrate 12.

On the other hand, unlike the first reinforcing substrate 40, the second reinforcing substrate 42 does not need to be deflected, and it is necessary to secure the stiffness of the TFT substrate 12 in a state in which the flexible cable 112 is connected. For that reason, the bending stiffness of the second reinforcing substrate 42 of the present embodiment is larger than the bending stiffness of the first reinforcing substrate 40.

Specifically, similar to the second reinforcing substrate 42, a material having a bending modulus of elasticity of 150 MPa or more and 2,500 MPa or less is preferably used for the first reinforcing substrate 40 of the present embodiment. From the above-described viewpoint, it is preferable that the bending stiffness of the first reinforcing substrate 40 is 540 Pacm$^4$ or more and 140000 Pacm$^4$ or less and is smaller than the bending stiffness of the second reinforcing substrate 42.

Additionally, similar to the second reinforcing substrate 42, the coefficient of thermal expansion of the first reinforcing substrate 40 is preferably closer to the coefficient of thermal expansion of the material of the conversion layer 14, and more preferably the ratio of the coefficient of thermal expansion of the first reinforcing substrate 40 to the coefficient of thermal expansion of the conversion layer 14 (the coefficient of thermal expansion of the first reinforcing substrate 40/the coefficient of thermal expansion of the conversion layer 14) is more preferably 0.5 or more and 2 or less. Moreover, from the viewpoint of elasticity, similar to the second reinforcing substrate 42, the first reinforcing substrate 40 preferably contains a material having a yield point.

As the material of the first reinforcing substrate 40, a material according to the method of peeling the first reinforcing substrate 40 in the first reinforcing substrate peeling step (refer to FIG. 6H), which will be described in detail below, is selected. However, in consideration of the viewpoint of the above characteristics, it is preferable that the material contains at least one of PET or PC.

Additionally, as illustrated in FIGS. 6D and 6E, the size of the surface of the first reinforcing substrate 40 of the present embodiment on the conversion layer 14 side is smaller than the size of the first surface 11A provided with the pixels 30 of the base material 11, and the terminal region 111 is not covered with the first reinforcing substrate 40.

Figure 6F:
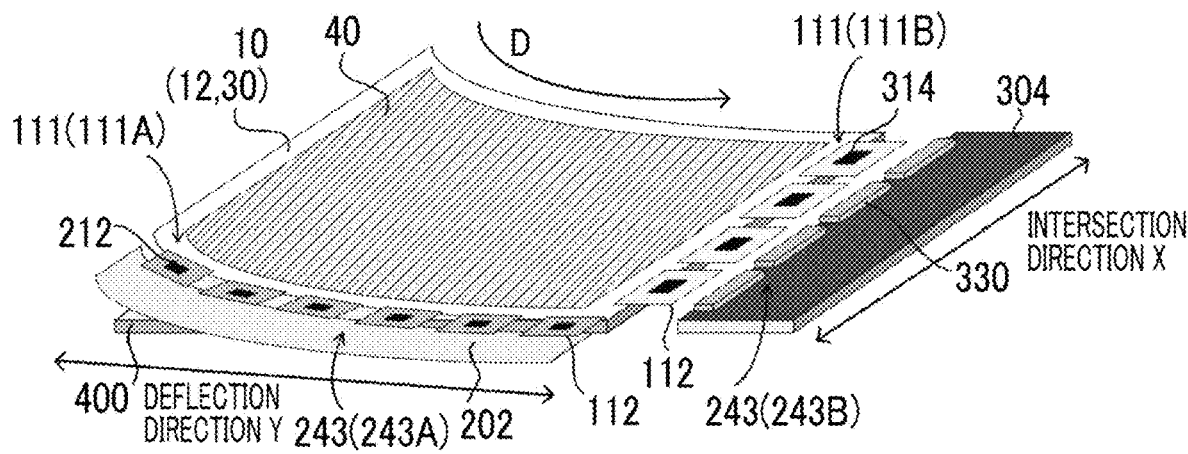
FIG. 6F is a view illustrating an example of a support body peeling step in an example of the method of manufacturing a radiation detector according to the embodiment.

Next, the radiation detector 10 is peeled from the support body 400 by the support body peeling step illustrated in FIG. 6F. As an example, in the present embodiment, the support body 400 is peeled by mechanical peeling. In a case where the peeling is performed by mechanical peeling, in the example illustrated in FIG. 6F, the side of the base material 11 of the TFT substrate 12 facing the side to which the flexible cable 112 is connected is set as the starting point of the peeling. The mechanical peeling is performed by peeling the TFT substrate 12 in a direction of arrow D illustrated in FIG. 6F from the support body 400 gradually from the side serving as the starting point toward the side to which the flexible cable 112 is connected, and the radiation detector 10 in a state where the flexible cable 112 is connected is obtained.

In addition, the side serving as the starting point of the peeling is preferably a side that intersects the longest side in a case where the TFT substrate 12 is viewed in a plan view. In other words, the side extending in the deflection direction Y in which the deflection is caused by the peeling is preferably the longest side in the TFT substrate 12. In the present embodiment, a side to which the driving substrate 202 is connected by the flexible cable 112 is longer than a side to which the signal processing substrate 304 is connected by the flexible cable 112. For that reason, the starting point of the peeling is used as a side facing a side where the terminal region 111 (111B) is provided.

In the present embodiment, after the TFT substrate 12 is further peeled from the support body 400, the flexible cable 112 of the radiation detector 10 and the connector 330 of the signal processing substrate 304 are electrically connected to each other.

Figure 6G:
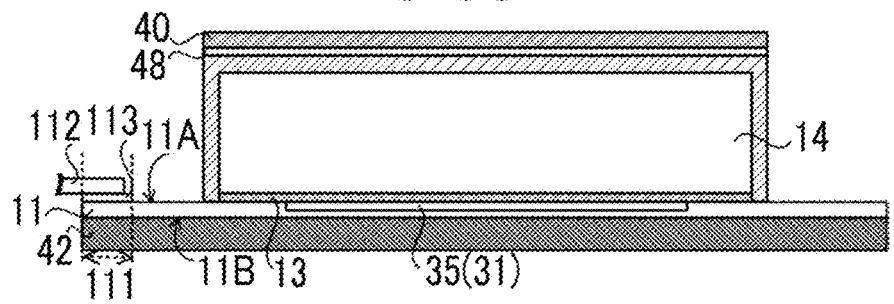
FIG. 6G is a view illustrating an example of a second reinforcing substrate disposing step in the example of the method of manufacturing a radiation detector according to the embodiment.

Next, the second reinforcing substrate 42 is provided on the TFT substrate 12 by a second reinforcing substrate disposing step illustrated in FIG. 6G. As an example, in the present embodiment, the second reinforcing substrate 42 provided with a pressure sensitive adhesive layer such as double-sided tape is bonded to the second surface 11B of the base material 11.

Figure 6H:
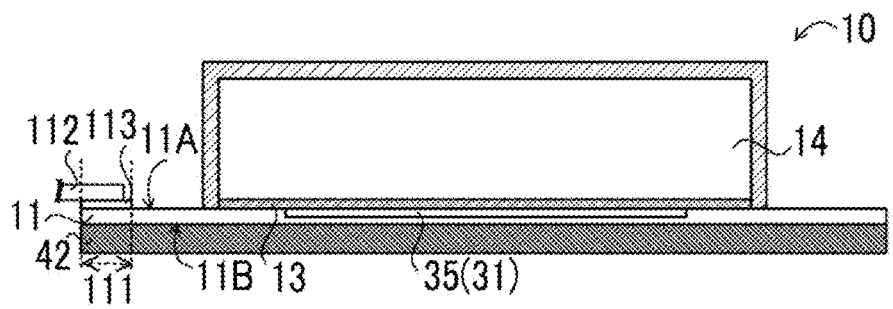
FIG. 6H is a view illustrating an example of a first reinforcing substrate peeling step in the example of the method of manufacturing a radiation detector according to the embodiment.

Next, the radiation detector 10 of the present embodiment is manufactured by peeling the first reinforcing substrate 40 from the TFT substrate 12 by the first reinforcing substrate peeling step illustrated in FIG. 6H.

As an example, in the present embodiment, a dismantleable adhesive of which the adhesiveness is lost by UV (ultraviolet) radiation is used as the adhesive layer 48, and the first reinforcing substrate 40 is peeled from the TFT substrate 12 by radiating UV from the surface of the first reinforcing substrate 40 opposite to the surface adhering to the TFT substrate 12 to lose the adhesiveness of the adhesive layer 48. Therefore, a material that transmits UV is used as the first reinforcing substrate 40 in the present form.

Next, the actions of the first reinforcing substrate 40 and the second reinforcing substrate 42 in the radiation detector 10 of the present embodiment will be described.

As described above, in the first reinforcing substrate 40, in a case where the TFT substrate 12 is peeled from the support body 400 in the support body peeling step (refer to FIG. 6F), the TFT substrate 12 is likely to be deflected because the base material 11 has flexibility. In a case where the TFT substrate 12 is largely deflected, there is a concern that a defect may occur in the TFT substrate 12. For example, there is a concern that the conversion layer 14 may be peeled from the TFT substrate 12, and particularly, an end part of the conversion layer 14 may be easily peeled from the TFT substrate 12. Additionally, for example, as a result of the TFT substrate 12 being largely deflected, there is a concern that the pixels 30 may be damaged.

In contrast, in the radiation detector 10 of the present embodiment, the first reinforcing substrate 40 is provided on the first surface 11A of the base material 11. For that reason, according to the radiation detector 10 of the present embodiment, it is possible to suppress that the TFT substrate 12 is largely deflected in a case where the TFT substrate 12 is peeled from the support body 400. Therefore, the radiation detector 10 of the present embodiment can suppress that a defect occurs in the TFT substrate 12.

Additionally, as illustrated in FIGS. 6D and 6E, the size of the surface of the first reinforcing substrate 40 of the present embodiment on the conversion layer 14 side is smaller than the size of the first surface 11A provided with the pixels 30 of the base material 11, and the first reinforcing substrate 40 does not cover the terminal region 111. For that reason, in the first reinforcing substrate peeling step (refer to FIG. 6H), in a case where the first reinforcing substrate 40 is peeled, it is possible to suppress that the flexible cable 112 connected to the terminal 113 of the terminal region 111 causes disconnection or is peeled.

Additionally, the present invention is not limited to a case where the TFT substrate 12 is peeled from the support body 400. Even in a case where the radiation detector 10 is handled as a single body during a manufacturing process of the radiographic imaging apparatus 1, there is a concern that a defect may occur in the TFT substrate 12 similarly to the above due to the deflection of the TFT substrate 12. In contrast, in the method of manufacturing the radiation detector 10 of the present embodiment, the first reinforcing substrate peeling step is performed after the second reinforcing substrate disposing step. Therefore, at least one of the first reinforcing substrate 40 or the second reinforcing substrate 42 is provided on the TFT substrate 12. For that reason, according to the radiation detector 10 of the present embodiment, even in a case where the radiation detector 10 is handled as a single body, it is possible to suppress that the TFT substrate 12 is largely deflected, and it is possible to suppress that a defect occurs in the TFT substrate 12.

Additionally, in the method of manufacturing the radiation detector 10 of the present embodiment, the first reinforcing substrate 40 is peeled by the first reinforcing substrate peeling step (refer to FIG. 6H). Therefore, a finally obtained radiation detector 10 does not include the first reinforcing substrate 40. Meanwhile, it is generally known that the bending stiffness is proportional to the third power of the thickness of an object.

Here, a radiographic imaging apparatus (refer to FIGS. 7A and 8A, a housing 120 and the radiographic imaging apparatus 1) in which a radiation detector 10, which is different from the radiation detector 10 of the present embodiment, is housed in a housing is considered as a comparative example. The radiation detector 10 is in a state in which both the first reinforcing substrate 40 and the second reinforcing substrate 42 are provided on the TFT substrate 12 as in the state illustrated in FIG. 6G. In this way, the bending stiffness is secured by the first reinforcing substrate 40 and the second reinforcing substrate 42 in a state in which both the first reinforcing substrate 40 and the second reinforcing substrate 42 are provided on the TFT substrate 12. The bending stiffness obtained by the first reinforcing substrate 40 and the second reinforcing substrate 42 is proportional to a value $(T1^3+T2^3)$ obtained by adding the third power of a thickness T1 and the third power of a thickness T2 together in a case where the thickness of the first reinforcing substrate 40 is T1 and the thickness of the second reinforcing substrate 42 is T2.

On the other hand, in the radiation detector 10 of the present embodiment, the bending stiffness is secured by the second reinforcing substrate 42 in a state in which only the second reinforcing substrate 42 is provided on the TFT substrate 12 as in a state illustrated in FIGS. 2, 3, and 6H and the like. Here, in a case where the thickness of the housing (refer to a housing 120 in FIGS. 7A and 8A) that houses the radiation detector 10 is the same as that of the above comparative example, the thickness of the second reinforcing substrate 42 can be a thickness (T1+T2) obtained by adding the thickness T1 and the thickness T2 together. The bending stiffness obtained by the second reinforcing substrate 42 in this case is proportional to the third power of a value $((T1+T2)^3)$ obtained by adding the thickness T1 and the thickness T2.

The third power $((T1+T2)^3)$ of the value obtained by adding the thickness T1 and the thickness T2 is larger than a value $(T1^3+T2^3)$ obtained by adding the third power of the thickness T1 and the third power of the thickness T2 together $((T1+T2)^3 > T1^3+T2^3)$. Therefore, the bending stiffness of the radiation detector 10 of the present embodiment is higher than that in the case of the above comparative example.

Meanwhile, in a case where the bending stiffness secured by both the first reinforcing substrate 40 and the second reinforcing substrate 42 in the above comparative example is to be obtained by the second reinforcing substrate 42, the thickness of the second reinforcing substrate 42 is the third power root of the value $(T1^3+T2^3)$ obtained by adding the third power of the thickness T1 and the third power of the thickness T2 together, that is, $(T1^3+T2^3)^{1/3}$.

The third power root of the value $(T1^3+T2^3)$ obtained by adding the third power of the thickness T1 and the third power of the thickness T2 together is smaller than the value (T1+T2) obtained by adding the thickness T1 and the thickness T2 together $((T1+T2) > (T1^3+T2^3)^{1/3})$. That is, the thickness ((third power root of $(T1^3+T2^3)$)) of the entire reinforcing substrate in a case where only the second reinforcing substrate 42 is provided is smaller than the thickness (T1+T2) of the entire reinforcing substrates when the first reinforcing substrate 40 and the second reinforcing substrate 42 are provided. Therefore, as compared to the case of the above comparative example, the radiation detector 10 of the present embodiment can reduce the thickness of the entire radiation detector 10.

Additionally, in the radiation detector 10 of the present embodiment, the position of a stress neutral plane generated in a case where the radiation detector 10 is deflected can be adjusted by the second reinforcing substrate 42. The "stress neutral plane" in the radiation detector 10 is a plane in which the radiation detector does not expand or contract even in a case where the radiation detector is deflected, and the stress is 0 in the stress neutral plane. As stress is applied to an interface between the TFT substrate 12 and the conversion layer 14, the conversion layer 14 is easily peeled from the TFT substrate 12. In addition, in the present embodiment, the "interface" refers to the surface of the conversion layer 14 facing the TFT substrate 12. Therefore, the closer the stress neutral plane in a case where the radiation detector 10 is deflected to the interface between the TFT substrate 12 and the conversion layer 14, the smaller the stress applied to the interface between the TFT substrate 12 and the conversion layer 14, and the conversion layer 14 is not easily peeled from the TFT substrate 12.

In a case where the TFT substrate 12 is deflected, the position of the stress neutral plane is determined depending on the total thickness, and in a case where a thickness above the interface between the TFT substrate 12 and the conversion layer 14 and a thickness below the interface are the same, it can be considered that the position of the stress neutral plane and the position of the interface between the TFT substrate 12 and the conversion layer 14 coincide with each other.

In the radiation detector 10 of the present embodiment, the thickness of the conversion layer 14 above the interface between the TFT substrate 12 and the conversion layer 14 is relatively large, and the thickness of the TFT substrate 12 below the interface between the TFT substrate 12 and the conversion layer 14 is relatively small. For that reason, in the radiation detector 10, by providing the second reinforcing substrate 42 to increase the thickness below the interface between the TFT substrate 12 and the conversion layer 14, the position of the stress neutral plane can be adjusted and brought closer to the interface between the TFT substrate 12 and the conversion layer 14. In addition, in the middle of the manufacturing process of manufacturing the radiation detector 10, it is preferable that the thickness of the second reinforcing substrate 42 is larger than the thickness of the first reinforcing substrate 40 in order to bring the stress neutral plane closer to the interface between the TFT substrate 12 and the conversion layer 14 even in a state in which both the first reinforcing substrate 40 and the second reinforcing substrate 42 are provided (refer to FIG. 6G).

In this way, according to the radiation detector 10, the position of the stress neutral plane can be adjusted and brought closer to the interface between the TFT substrate 12 and the conversion layer 14 by the second reinforcing substrate 42. Therefore, it is possible to suppress that a defect occurs in the TFT substrate 12 even in a case where the TFT substrate 12 is deflected.

Additionally, in the radiation detector 10 of the present embodiment, there is a concern that the flexible cable 112 may be peeled from the terminal region 111 of the base material 11 or the connection deviation may be caused. In particular, in a case where the TFT substrate 12 is deflected in the support body peeling step (refer to FIG. 6F), the flexible cable 112 is easily peeled from the terminal region 111 of the base material 11 or causes a disconnection.

Additionally, in a case where the radiation detector 10 is handled as a single body in the middle of the manufacturing process of the radiographic imaging apparatus 1 not limited to the support body peeling step (refer to FIG. 6F), there is a concern that the TFT substrate 12 may be deflected and thereby the flexible cable 112 may be peeled from the terminal region 111 of the base material 11 or cause a disconnection. In a case where the flexible cable 112 is peeled from the terminal region 111 of the base material 11 or the connection deviation is caused, it is necessary to rework the flexible cable 112 to the terminal region 111.

In contrast, in the radiation detector 10 of the present embodiment, as described above, the first reinforcing substrate 40 covers a part of the first surface 11A of the base material 11 (TFT substrate 12) and does not cover the terminal region 111. For that reason, in the radiation detector 10 of the present embodiment, in a case where the flexible cable 112 is reworked in the terminal region 111 in a state in which the first reinforcing substrate 40 is provided, the reworking can be performed without being blocked by the first reinforcing substrate 40. Therefore, the peeling property in the reworking process is excellent. Additionally, in a case where the flexible cable 112 is reworked after the first reinforcing substrate 40 is peeled, the radiation detector 10 is provided with the second reinforcing substrate 42, and the stiffness is secured by the second reinforcing substrate 42. Therefore, the peeling property in the reworking process is excellent.

In addition, the timing at which the wiring connection step (refer to FIG. 6C) is performed is not limited to a timing exemplified in the present embodiment. For example, the wiring connection step (refer to FIG. 6C) may be performed at a timing between the first reinforcing substrate disposing step (refer to FIGS. 6D and 6E) and the support body peeling step (refer to FIG. 6F).

Additionally, for example, the wiring connection step (refer to FIG. 6C) may be performed at a timing after the first reinforcing substrate peeling step (refer to FIG. 6H). In this case, there is no concern that the flexible cable 112 may cause a disconnection or the like in the first reinforcing substrate peeling step (refer to FIG. 6H). Additionally, in a case where the reworking of the flexible cable 112 is performed, the first reinforcing substrate 40 does not become an obstacle even in a case where the size of the surface of the first reinforcing substrate 40 on the conversion layer 14 side is not smaller than the size of the first surface 11A of the base material 11. For that reason, in a case where the wiring connection step (refer to FIG. 6C) is performed at a timing after the first reinforcing substrate peeling step (refer to FIG. 6H), the position and size of the terminal region 111 and the peeling property in the reworking process of the flexible cable 112 may not have to be considered with respect to the size of the first reinforcing substrate 40. For example, the size of the surface of the first reinforcing substrate 40 on the conversion layer 14 side may be equal to or larger than the size of the first surface 11A of the base material 11, and for example, the terminal region 111 may be covered with the first reinforcing substrate 40.

In addition, for example, the mechanical peeling may be performed after the flexible cable 112 of the radiation detector 10 and the connector 330 of the signal processing substrate 304 are electrically connected to each other.

In addition, the radiation detectors 10 of the present embodiment may be applied to an ISS type radiographic imaging apparatus or may be applied to a penetration side sampling (PSS) type radiographic imaging apparatus in which radiation is radiated from the conversion layer 14 side.

Figure 7A:
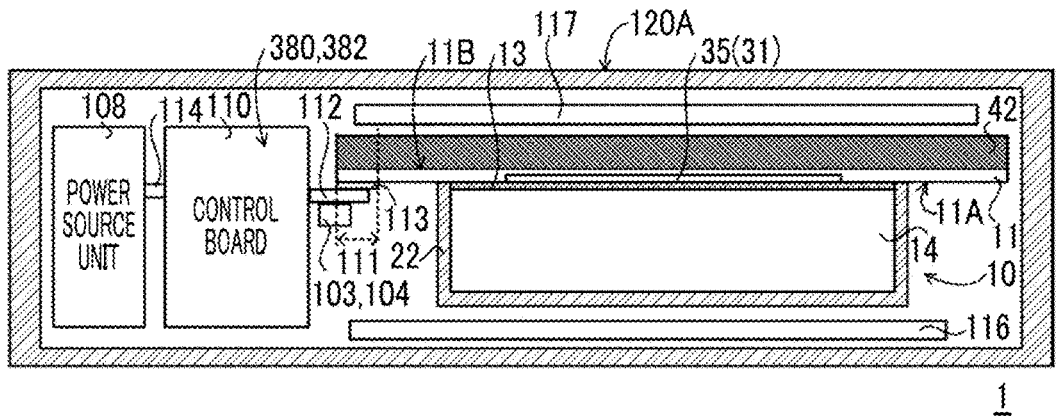
FIG. 7A is a cross-sectional view illustrating a cross section of an example of a radiographic imaging apparatus to which the radiation detector of the embodiment is applied.
Figure 7B:
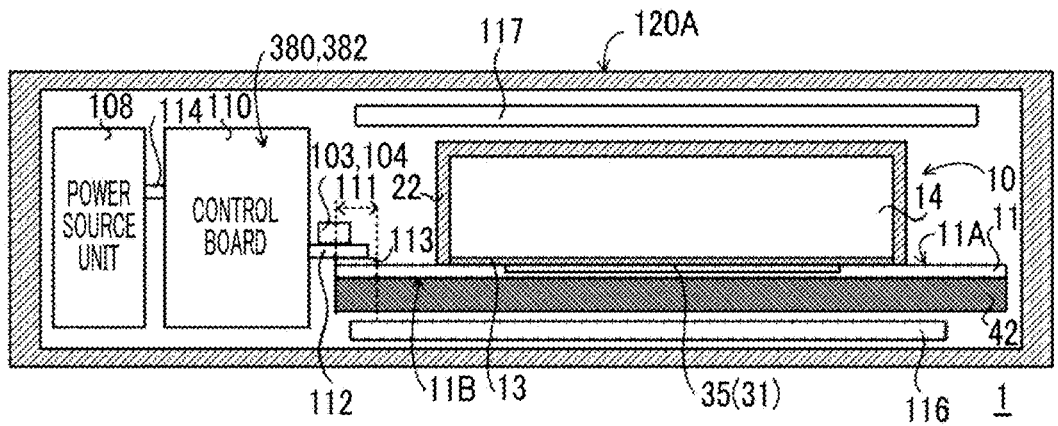
FIG. 7B is a cross-sectional view illustrating a cross section of an example of a radiographic imaging apparatus to which the radiation detector of the embodiment is applied.

A cross-sectional view of an example in a state in which the radiation detector 10 of the present embodiment is applied to the ISS type radiographic imaging apparatus 1 is illustrated in FIG. 7A. Additionally, a cross-sectional view of another example in a state where the radiation detector 10 of the present embodiment is applied to the PSS type radiographic imaging apparatus 1 is illustrated in FIG. 7B.

As illustrated in FIG. 7A, the radiation detector 10, the power source unit 108, and a control board 110 are provided side by side in a direction intersecting an incidence direction of radiation within the housing 120. In the example illustrated in FIG. 7A, the radiation detector 10 is provided in a state where a side where the conversion layer 14 of the pixel array 31 is not provided faces an imaging surface 120A side of the housing 120 that is irradiated with radiation transmitted through the subject. On the other hand, in the example illustrated in FIG. 7B, the radiation detector 10 is provided in a state in which the conversion layer 14 faces the imaging surface 120A. The imaging surface 120A of the present embodiment is an example of the irradiation surface of the present disclosure.

The control board 110 is a board in which an image memory 380 for storing image data according to the electric charges read out from the pixels 30 of the pixel array 31, and a control unit 382 for controlling reading-out or the like of the electric charges from the pixels 30, and the like are formed. The control board 110 is electrically connected to the pixels 30 of the pixel array 31 by the flexible cable 112 including a plurality of signal wiring lines. In addition, in the radiographic imaging apparatus 1 illustrated in FIGS. 7A and 7B, the control board 110 is a so-called chip on film (COF) in which a drive unit 103 for controlling the switching states of the TFTs 32 of the pixels 30 under the control of the control unit 382, and a signal processing unit 104 for creating and outputting image data according to the electric charges read out from the pixels 30 are provided on the flexible cable 112. However, at least one of the drive unit 103 or the signal processing unit 104 may be formed in the control board 110.

Additionally, the control board 110 is connected to the power source unit 108, which supplies electrical power to the image memory 380, the control unit 382, and the like that are formed in the control board 110, by a power source line 114.

The housing 120 is preferably lightweight, has a low absorbance of radiation R, particularly X-rays, and has a high stiffness, and is preferably made of a material having a sufficiently high modulus of elasticity. As the material of the housing 120, it is preferable to use a material having a bending modulus of elasticity of 10,000 MPa or more. As the material of the housing 120, carbon or carbon fiber reinforced plastics (CFRP) having a bending modulus of elasticity of about 20,000 to 60,000 MPa can be suitably used.

In the capturing of a radiographic image by the radiographic imaging apparatus 1, a load from a subject is applied to the imaging surface 120A of the housing 120. In a case where the stiffness of the housing 120 is insufficient, there are concerns that a defect may occur such that the TFT substrate 12 is deflected due to the load from the subject and the pixels 30 are damaged. By housing the radiation detector 10 inside the housing 120 made of a material having a bending modulus of elasticity of 10,000 MPa or more, it is possible to suppress the deflection of the TFT substrate 12 due to the load from the subject.

A sheet 116 is further provided on a side from which the radiation transmitted through the radiation detector 10 is emitted, within the housing 120 of the radiographic imaging apparatus 1 illustrated in FIGS. 7A and 7B. The sheet 116 is, for example, a copper sheet. The copper sheet does not easily generate secondary radiation due to incident radiation, and therefore, has a function of preventing scattering to the rear side, that is, the conversion layer 14 side. In addition, it is preferable that the sheet 116 covers at least an entire surface of the conversion layer 14 from which radiation is emitted, and covers the entire conversion layer 14.

Additionally, a protective layer 117 is further provided on a side (imaging surface 120A side) on which radiation is incident, within the housing 120 of the radiographic imaging apparatus 1 illustrated in FIGS. 7A and 7B. As the protective layer 117, moistureproof films, such as an ALPET (registered trademark) sheet obtained by laminating aluminum, for example by adhering aluminum foil, to the insulating sheet (film), a Parylene (registered trademark) film, and an insulating sheet (film), such as polyethylene terephthalate, can be applied. The protective layer 117 has a moistureproof function and an antistatic function with respect to the pixel array 31. For that reason, it is preferable that the protective layer 117 covers at least the entire surface of the pixel array 31 on the side on which radiation is incident, and it is preferable to cover the entire surface of the TFT substrate 12 on the side on which radiation is incident.

In addition, although FIGS. 7A and 7B illustrates a form in which both the power source unit 108 and the control board 110 are provided on one side of the radiation detector 10, specifically, on one side of a rectangular pixel array 31, a position where the power source unit 108 and the control board 110 are provided is not limited to the form illustrated in FIGS. 7A and 7B. For example, the power source unit 108 and the control board 110 may be provided so as to be respectively distributed onto two facing sides of the pixel array 31 or may be provided so as to be respectively distributed onto two adjacent sides.

Figure 7C:
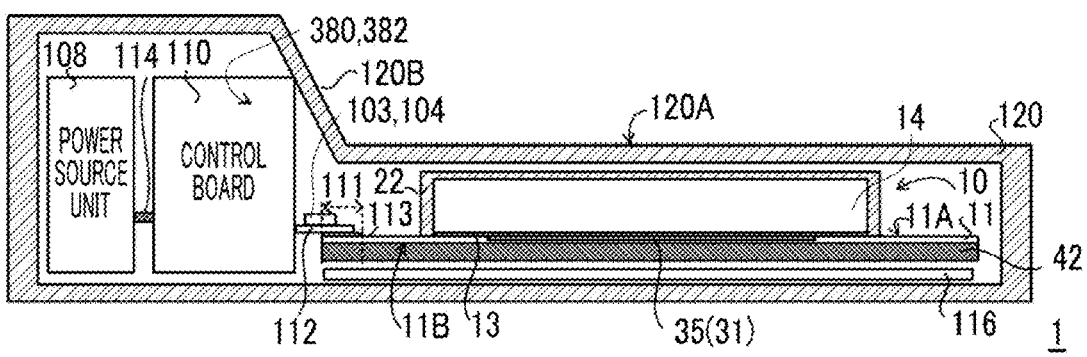
FIG. 7C is a cross-sectional view illustrating a cross section of an example of a radiographic imaging apparatus to which the radiation detector of the embodiment is applied.

Meanwhile, there are many cases where each of the power source unit 108 and the control board 110 is thicker than the radiation detector 10. In such a case, as in the example illustrated in FIG. 7C, the thickness of the portion of the housing 120 in which the radiation detector 10 is provided may be smaller than the thickness of the portion of the housing 120 in which each of the power source unit 108 and the control board 110 is provided. In addition, in this way, in a case where the thickness of the portion of the housing 120 in which each of the power source unit 108 and the control board 110 is provided and the thickness of the portion of the housing 120 in which the radiation detector 10 is provided are made different, and in a case where a step is generated at a boundary part between the two portions, there is a concern that a sense of discomfort may be given to a subject who comes into contact with a boundary part 120B. Therefore, the form of the boundary part 120B is preferably in a state of having an inclination.

Accordingly, it is possible to construct an ultra-thin portable electronic cassette according to the thickness of the radiation detector 10.

Additionally, for example, in this case, the materials of the housing 120 may be different in the portion of the housing 120 in which each of the power source unit 108 and the control board 110 is provided and the portion of the housing 120 in which the radiation detector 10 is provided. Moreover, for example, the portion of the housing 120 in which each of the power source unit 108 and the control board 110 is provided and the portion of the housing 120 in which the radiation detector 10 is provided may be separated configured.

Additionally, as described above, the housing 120 is preferably made of a material having a low absorbance of radiation R, particularly X-rays and a high stiffness, and is preferably made of a material having a sufficiently high modulus of elasticity. However, as in the example illustrated in FIG. 7D, a portion 120C corresponding to the imaging surface 120A of the housing 120 may be made of a material having a low absorbance of the radiation R, a high stiffness, and a sufficiently high modulus of elasticity, and the other portions may be made of a material different from the portion 120C, for example, a material having a lower modulus of elasticity than the portion 120C.

Figure 7D:
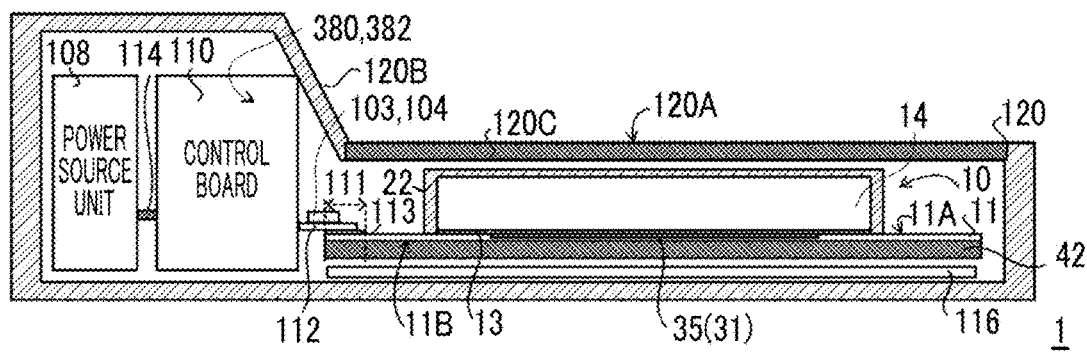
FIG. 7D is a cross-sectional view illustrating a cross section of an example of a radiographic imaging apparatus to which the radiation detector of the embodiment is applied.
Figure 7E:
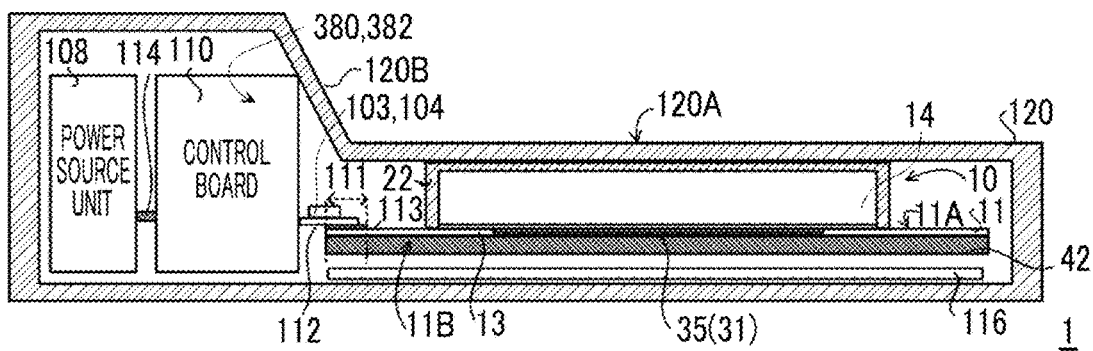
FIG. 7E is a cross-sectional view illustrating a cross section of an example of a radiographic imaging apparatus to which the radiation detector of the embodiment is applied.

Additionally, as in the example illustrated in FIG. 7D, the radiation detector 10 and the inner wall surface of the housing 120 may be in contact with each other. In this case, the radiation detector 10 and the inner wall surface of the housing 120 may be adhered to each other via an adhesive layer, or may simply be in contact with each other without an adhesive layer. Since the radiation detector 10 and the inner wall surface of the housing 120 are in contact with each other in this way, the stiffness of the radiation detector 10 is further secured.

Figure 8A:
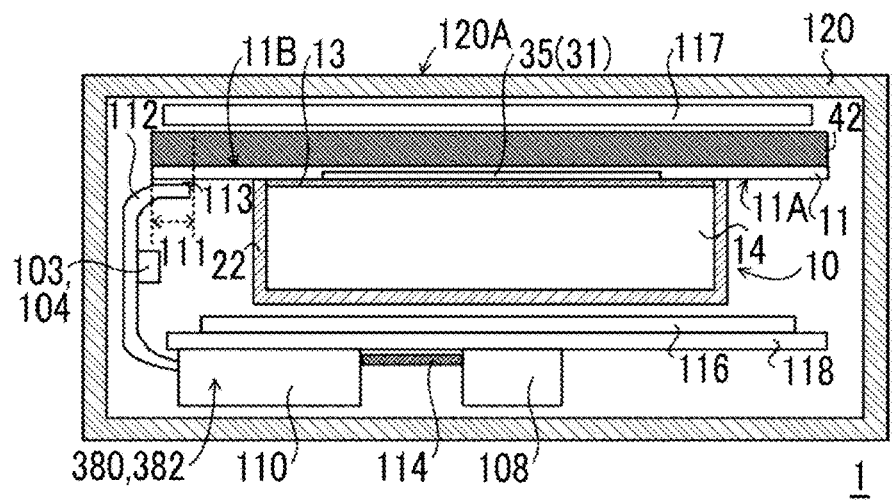
FIG. 8A is a cross-sectional view illustrating a cross section of another example of the radiographic imaging apparatus to which the radiation detector of the embodiment is applied.

Additionally, a cross-sectional view of another example in a state in which the radiation detector 10 of the present embodiment is applied to the ISS type radiographic imaging apparatus 1 is illustrated in FIG. 8A. Moreover, a cross-sectional view of another example in a state where the radiation detector 10 of the present embodiment is applied to the PSS type radiographic imaging apparatus 1 is illustrated in FIG. 8B.

Figure 8B:
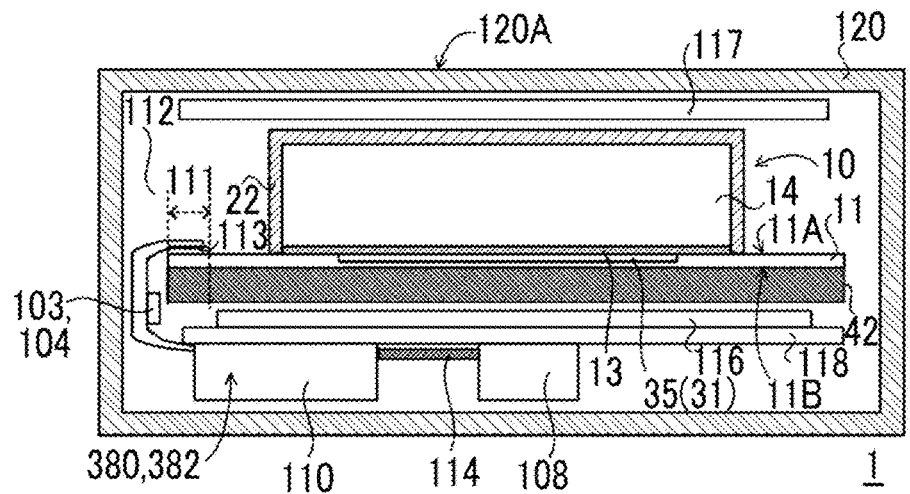
FIG. 8B is a cross-sectional view illustrating a cross section of another example of the radiographic imaging apparatus to which the radiation detector of the embodiment is applied.

As illustrated in FIGS. 8A and 8B, the power source unit 108 and the control board 110 are provided side by side in the direction intersecting the incidence direction of radiation within the housing 120, and the radiation detector 10, the power source unit 108, and the control board 110 are provided side by side in the incidence direction of radiation.

Additionally, in the radiographic imaging apparatus 1 illustrated in FIGS. 8A and 8B, a base 118 that supports the radiation detector 10 and the control board 110 is provided between the control board 110 and the power source unit 108, and the sheet 116. For example, carbon or the like is used for the base 118.

According to this configuration illustrated in FIGS. 8A and 8B, the size of the radiographic imaging apparatus 1 in a plan view can be reduced as compared to a case where the radiation detector 10, the control board 110, and the power source unit 108 are disposed side by side in the transverse direction in the figure (refer to FIGS. 7A to 7E).

As described above, the radiation detector 10 of the present embodiment includes the TFT substrate 12 in which the plurality of pixels 30 are formed in the pixel region 35 of the first surface 11A of the base material 11, the conversion layer 14, and the second reinforcing substrate 42. Additionally, the method of manufacturing the radiation detector 10 includes the substrate forming step, the conversion layer forming step, the first reinforcing substrate disposing step, the support body peeling step, the second reinforcing substrate disposing step, and the first reinforcing substrate peeling step.

In the substrate forming step, the flexible base material 11 is provided on the support body 400 via the peeling layer 102, and the TFT substrate 12 provided having the plurality of pixels 30 for accumulating electric charges generated depending on light converted from the radiation R is formed in the pixel region 35 of the base material 11. In the conversion layer forming step, the conversion layer 14 that converts the radiation R into light is formed on the first surface 11A provided with the pixels 30 of the base material 11. In the first reinforcing substrate disposing step, the first reinforcing substrate 40 is provided on the surface of the conversion layer 14 opposite to the surface on the TFT substrate 12 side. In the support body peeling step, the TFT substrate 12 provided with the conversion layer 14 and the first reinforcing substrate 40 is peeled from the support body 400. In the second reinforcing substrate disposing step, the second reinforcing substrate 42 is provided on the second surface 11B of the TFT substrate 12 peeled from the support body 400, which is the surface peeled from the support body 400. In the first reinforcing substrate peeling step, after the second reinforcing substrate disposing step, the first reinforcing substrate 40 is peeled from the TFT substrate 12 provided with the conversion layer 14.

As described above, in the method of manufacturing the radiation detector 10 of the present embodiment, the first reinforcing substrate disposing step, the support body peeling step, the second reinforcing substrate disposing step, and the first reinforcing substrate peeling step are sequentially performed. Therefore, it is possible to suppress that a defect occurs in the TFT substrate 12, and the peeling property in the reworking process is excellent.

In addition, the radiation detector 10 and the method of manufacturing the radiation detector 10 are not limited to the forms described in the above respective embodiment.

For example, the method of peeling the first reinforcing substrate 40 in the first reinforcing substrate peeling step is not limited to the radiation of UV. For example, a method may be used in which the adhesive layer 48 made of a dismantleable adhesive of which the adhesiveness is lost by heating is provided and the first reinforcing substrate 40 is peeled from the TFT substrate 12 by heating. In addition, a method that does not easily affect the TFT substrate 12 and the like is preferable, and a method that does not easily affect the protective layer 22 that is in contact with the adhesive layer 48 is particularly preferable. For that reason, it is preferable to perform the peeling by the radiation of UV rather than the peeling by heating. In a case where the first reinforcing substrate 40 is peeled by heating, a material that does not transmit UV may be used for the first reinforcing substrate 40. For example, carbon or the like may be used for the first reinforcing substrate 40. In addition, in this case, the first reinforcing substrate 40 can be reused in the manufacture of the radiation detector 10.

Additionally, in the present embodiment, since the conversion layer 14 is CsI and CsI is hard and brittle (weak to deflection), the bending stiffness of the second reinforcing substrate 42 is high, for example, 100 times or more the bending stiffness of the base material 11. However, in a case where another material, for example, a material that is stronger to deflection than CsI, such as GOS, is used for the conversion layer 14, the bending stiffness of the second reinforcing substrate 42 may be lower than the above-described bending stiffness. Additionally, the smaller the thickness of the conversion layer 14 and the smaller the size of the pixel 30, the second reinforcing substrate 42 is not easily damaged in the case of being deflected. Therefore, the bending stiffness of the second reinforcing substrate 42 can be relatively reduced. In this way, the bending stiffness of the second reinforcing substrate 42 may be determined depending on the resistance of the conversion layer 14 and the pixels 30 to deflection.

Additionally, in the above-described support body peeling step, the step of peeling the TFT substrate 12 from the support body 400 by the mechanical peeling has been described. However, the peeling method is not limited to the described form. For example, a form of performing so-called laser peeling of peeling the TFT substrate 12 by radiating a laser beam from the surface of the support body 400 opposite to the side on which the TFT substrate 12 is formed may be adopted.

Figure 9:
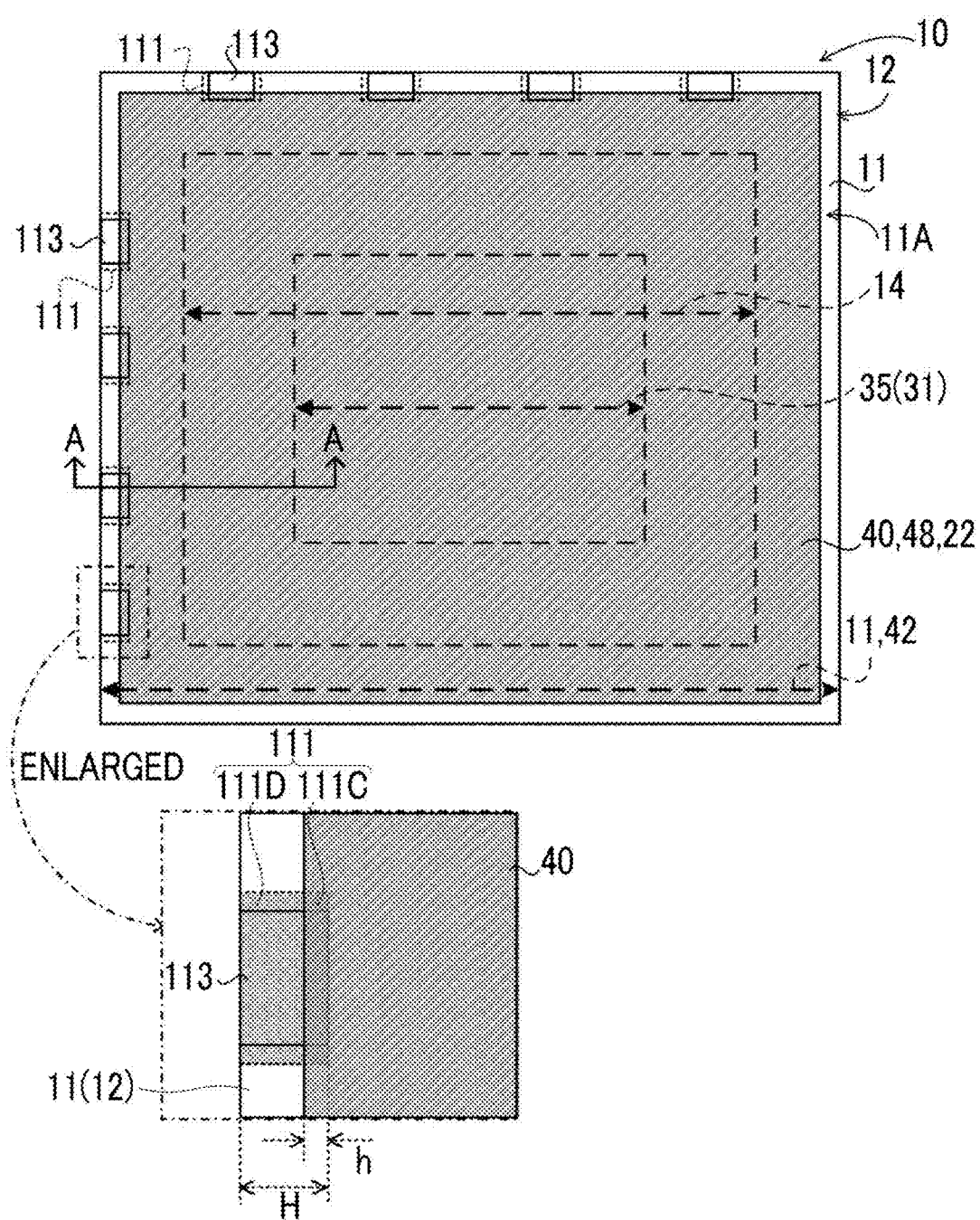
FIG. 9 is a plan view of an example of the radiation detector of the embodiment as seen from the side on which a conversion layer is provided.
Figure 10:
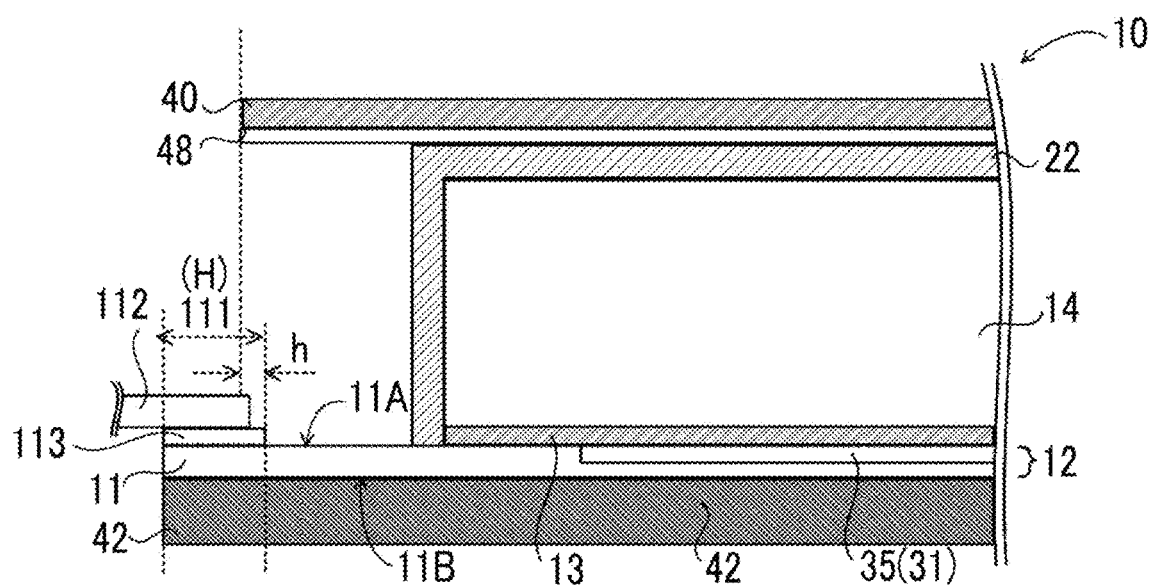
FIG. 10 is a cross-sectional view taken along line A-A of the radiation detector illustrated in FIG. 9.

Additionally, the size and shape of the first reinforcing substrate 40 are not limited to the above-described forms (refer to FIGS. 6D and 6E). For example, the first reinforcing substrate 40 may cover a partial region of the terminal region 111. FIG. 9 is a plan view of the radiation detector 10 having a form in which the first reinforcing substrate 40 covers a partial region of the terminal region 111, as viewed from the first surface 11A side of the base material 11. Additionally, FIG. 10 is a cross-sectional view taken along line A-A of the radiation detector 10 in FIG. 9.

As described above, it is more preferable that the size of the surface of the first reinforcing substrate 40 on the conversion layer 14 is larger in terms of securing the stiffness. However, in a case where the entire terminal region 111 is covered, the first reinforcing substrate 40 becomes an obstacle and the peeling property in the reworking process of the flexible cable 112 may deteriorate. Thus, in the radiation detector 10 illustrated in FIGS. 9 and 10, the first reinforcing substrate 40 covers a partial region of the terminal region 111. Specifically, the terminal region 111 has a first region 111C covered with the first reinforcing substrate 40 and a second region 111D not covered with the first reinforcing substrate 40.

As the size (area) of the first region 111C is larger, in other words, the portion of the terminal region 111 covered with the first reinforcing substrate 40 is larger, the concern that the peeling property in the reworking process may deteriorate is higher. In a case where the peeling property in the reworking process is considered, the size of the first region 111C is preferably smaller than the size of the second region 111D. Additionally, it is more preferable that a length h from one end part on an inner side of the base material 11 to the other end part on an outer edge side of the base material 11 in the first region 111C is ¼ or less (h≤¼×H) of a length H from one end part on the inner side of the base material 11 to the other end part on the outer edge side of the base material 11 in the terminal region 111.

Figure 11:
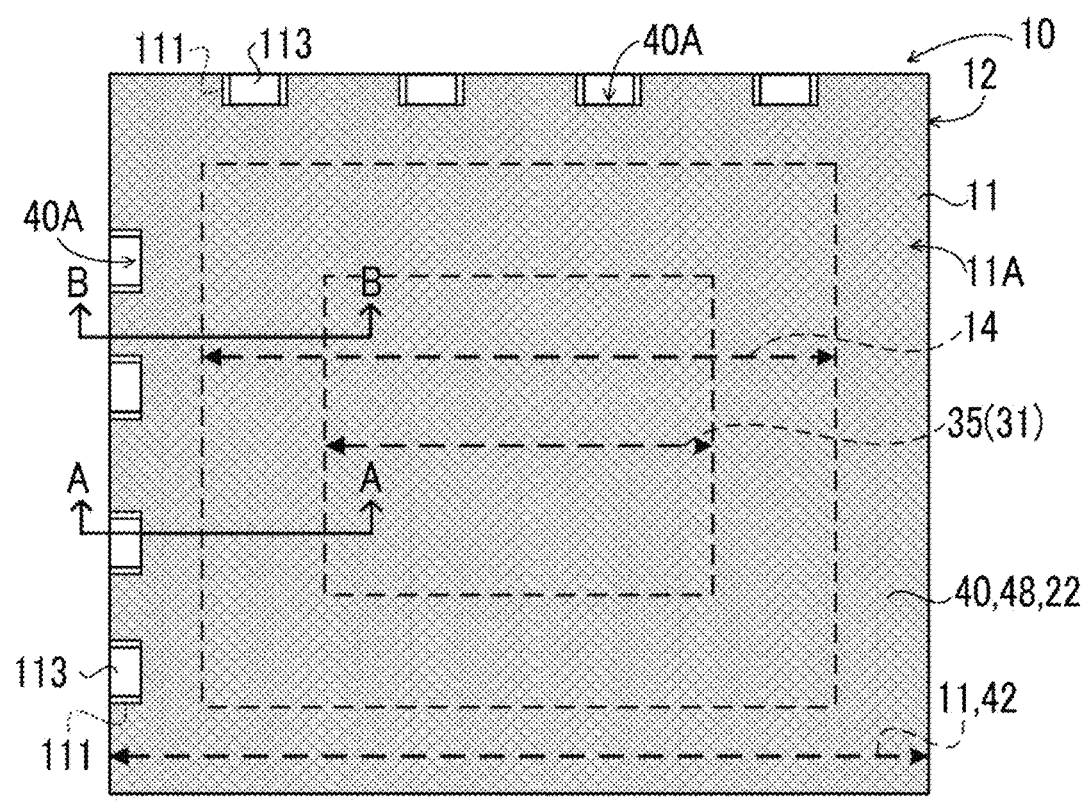
FIG. 11 is a plan view of an example of the radiation detector of the embodiment as seen from the side on which a conversion layer is provided.

Additionally, for example, the first reinforcing substrate 40 may cover the entire region of the base material 11 (TFT substrate 12) other than the terminal region 111. FIG. 11 is a plan view of the radiation detector 10 having a form in which the first reinforcing substrate 40 covers the entire region of the base material 11 other than the terminal region 111, as viewed from the first surface 11A side of the base material 11. Additionally, FIG. 12A is a cross-sectional view taken along line A-A of the radiation detector 10 in FIG. 11 and FIG. 12B is a cross-sectional view taken along line B-B of the radiation detector 10 in FIG. 11.

Figure 12A:
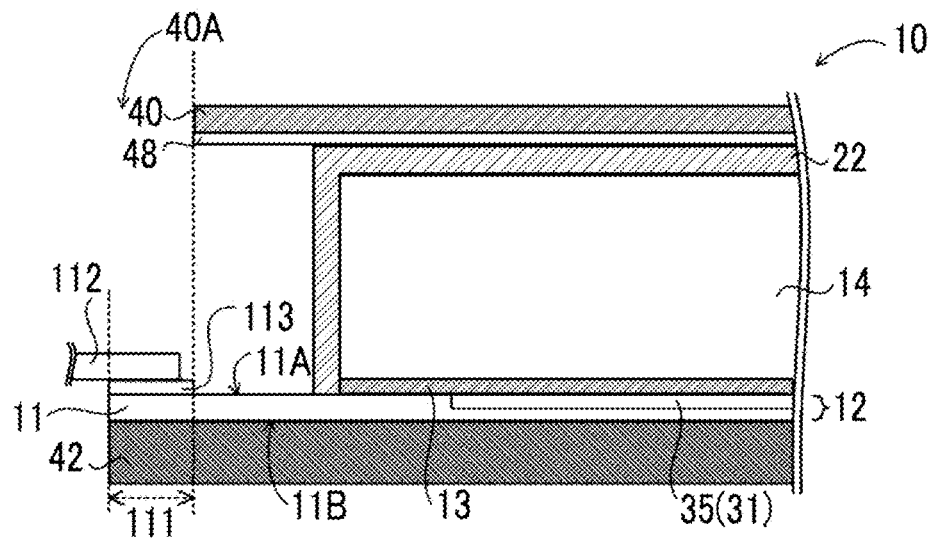
FIG. 12A is a cross-sectional view taken along line A-A of the radiation detector illustrated in FIG. 11.

As illustrated in FIGS. 11 and 12A, the first reinforcing substrate 40 is provided with a cutout part 40A at a position corresponding to the terminal region 111 and does not cover a region corresponding to the terminal region 111. Meanwhile, as illustrated in FIGS. 11 and 12B, the first reinforcing substrate 40 covers a portion up to the end part (outer edge) of the base material 11 (TFT substrate 12) in a region where the terminal region 111 is not provided.

Figure 12B:
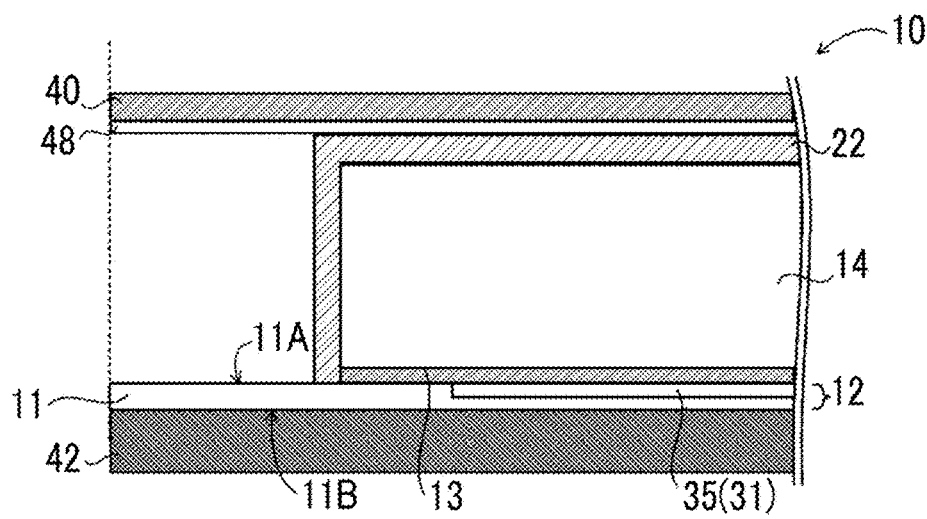
FIG. 12B is a cross-sectional view taken along line B-B of the radiation detector illustrated in FIG. 11.

In the radiation detector 10 illustrated in FIGS. 11, 12A, and 12B, by providing the cutout part 40A of the first reinforcing substrate 40 in the region corresponding to the terminal region 111, a region between a terminal region 111 and a terminal region 111 on the side of the base material 11 where terminal regions 111 are lined up is also covered with the first reinforcing substrate 40. For that reason, since the area of the first reinforcing substrate 40 covering the TFT substrate 12 (base material 11) is larger, higher stiffness can be secured. Additionally, since the terminal region 111 is not covered with the first reinforcing substrate 40, the peeling property in the reworking process of the flexible cable 112 does not deteriorate.

Additionally, the first reinforcing substrate 40 may have the following form.

In addition, in a case where the conversion layer 14 is formed by the vapor-phase deposition method, as illustrated in FIGS. 13 to 24, the conversion layer 14 of the present embodiment is formed with an inclination such that the thickness thereof gradually decreases toward an outer edge thereof. In the following, a central region of the conversion layer 14 where the thickness in a case where manufacturing errors and measurement errors are neglected can be considered to be substantially constant is referred to as a central part 14A. Additionally, an outer peripheral region of the conversion layer 14 having a thickness of, for example, 90% or less of the average thickness of the central part 14A of the conversion layer 14 is referred to as a peripheral edge part 14B. That is, the conversion layer 14 has an inclined surface that is inclined with respect to the TFT substrate 12 at the peripheral edge part 14B.

As illustrated in FIGS. 13 to 24, a pressure sensitive adhesive layer 60, a reflective layer 62, an adhesive layer 64, a protective layer 65, and the adhesive layer 48 may be provided between the conversion layer 14 and the first reinforcing substrate 40.

The pressure sensitive adhesive layer 60 covers the entire surface of the conversion layer 14 including the central part 14A and the peripheral edge part 14B of the conversion layer 14. The pressure sensitive adhesive layer 60 has a function of fixing the reflective layer 62 to the conversion layer 14. The pressure sensitive adhesive layer 60 preferably has optical transmittance. As materials of the pressure sensitive adhesive layer 60, for example, an acrylic pressure sensitive adhesive, a hot-melt pressure sensitive adhesive, and a silicone adhesive can be used. Examples of the acrylic pressure sensitive adhesive include urethane acrylate, acrylic resin acrylate, epoxy acrylate, and the like. Examples of the hot-melt pressure sensitive adhesive include thermoplastics, such as ethylene-vinyl acetate copolymer resin (EVA), ethylene-acrylate copolymer resin (EAA), ethylene-ethyl acrylate copolymer resin (EEA), and ethylene-methyl methacrylate copolymer (EMMA). The thickness of the pressure sensitive adhesive layer 60 is preferably 2 μm or more and 7 μm or less. By setting the thickness of the pressure sensitive adhesive layer 60 to 2 μm or more, the effect of fixing the reflective layer 62 on the conversion layer 14 can be sufficiently exhibited. Moreover, the risk of forming an air layer between the conversion layer 14 and the reflective layer 62 can be suppressed. When an air layer is formed between the conversion layer 14 and the reflective layer 62, there is a concern that multiple reflections may be caused in which the light emitted from the conversion layer 14 repeats reflections between the air layer and the conversion layer 14 and between the air layer and the reflective layer 62. Additionally, by setting the thickness of the pressure sensitive adhesive layer 60 to 7 μm or less, it is possible to suppress a decrease in modulation transfer function (MTF) and detective quantum efficiency (DQE).

The reflective layer 62 covers the entire surface of the pressure sensitive adhesive layer 60. The reflective layer 62 has a function of reflecting the light converted by the conversion layer 14. The reflective layer 62 is preferably made of an organic material. As the materials of the reflective layer 62, for example, white PET, $TiO_2$, $Al_2O_3$, foamed white PET, polyester-based high-reflection sheet, specular reflection aluminum, and the like can be used. The thickness of the reflective layer 62 is preferably 10 μm or more and 40 μm or less.

The adhesive layer 64 covers the entire surface of the reflective layer 62. The end part of the adhesive layer 64 extends to the surface of the TFT substrate 12. That is, the adhesive layer 64 adheres to the TFT substrate 12 at the end part thereof. The adhesive layer 64 has a function of fixing the reflective layer 62 and the protective layer 65 to the conversion layer 14. As the material of the adhesive layer 64, the same material as the material of the pressure sensitive adhesive layer 60 can be used, but the adhesive force of the adhesive layer 64 is preferably larger than the adhesive force of the pressure sensitive adhesive layer 60.

The protective layer 65 has a function equivalent to the protective layer 22 in the radiation detector 10 of each of the above-described embodiments and covers the entire surface of the adhesive layer 64. That is, the protective layer 65 is provided so as to cover the entire conversion layer 14 and covers a part of the TFT substrate 12 with the end part thereof. The protective layer 65 functions as a moistureproof film that prevents moisture from entering the conversion layer 14. As the material of the protective layer 65, for example, an organic film containing an organic material such as PET, PPS, OPP, PEN, or PI can be used. Additionally, as the protective layer 65, an Alpet (registered trademark) sheet may be used.

The first reinforcing substrate 40 is provided on the surface of the protective layer 65 via the adhesive layer 48. As the material of the adhesive layer 48, for example, it is possible to use the same material as the material of the pressure sensitive adhesive layer 60 and the adhesive layer 48.

Figure 13:
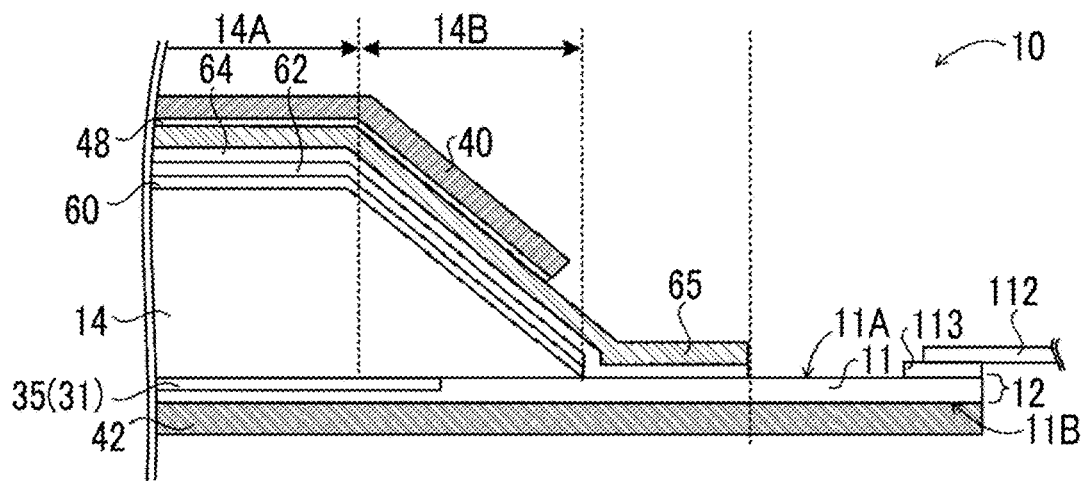
FIG. 13 is a cross-sectional view illustrating an example of a configuration of a radiation detector according to an embodiment of the disclosed technique.

In the example illustrated in FIG. 13, the first reinforcing substrate 40 extends to regions corresponding to the central part 14A and the peripheral edge part 14B of the conversion layer 14, and an outer peripheral part of the first reinforcing substrate 40 is bent in a state along the inclination at the peripheral edge part 14B of the conversion layer 14. The first reinforcing substrate 40 adheres to the protective layer 65 via the adhesive layer 48 in both a region corresponding to the central part 14A of the conversion layer 14 and a region corresponding to the peripheral edge part 14B of the conversion layer 14. In the example illustrated in FIG. 13, the end part of the first reinforcing substrate 40 is disposed in the region corresponding to the peripheral edge part 14B of the conversion layer 14.

Figure 14:
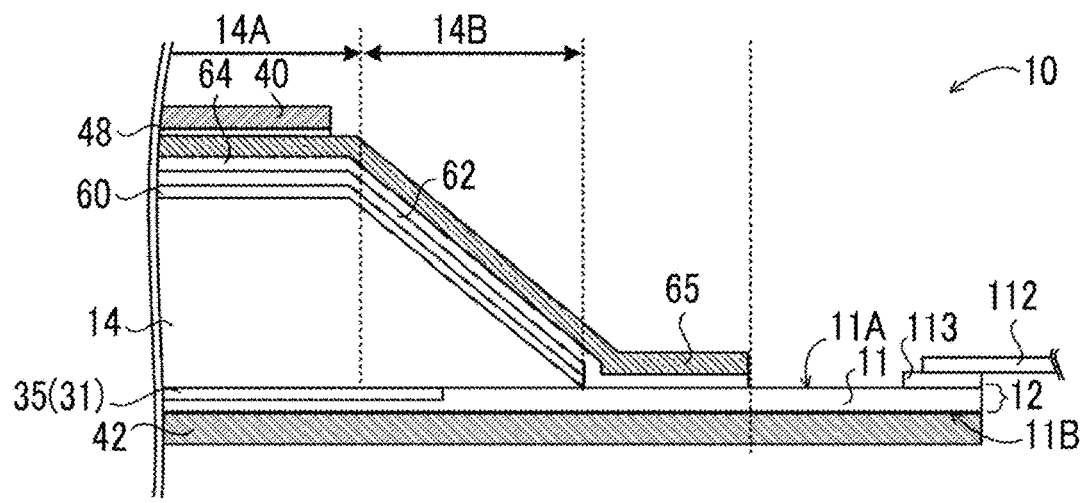
FIG. 14 is a cross-sectional view illustrating an example of a configuration of a radiation detector according to an embodiment of the disclosed technique.

As illustrated in FIG. 14, the first reinforcing substrate 40 may be provided only in the region corresponding to the central part 14A of the conversion layer 14. In this case, the first reinforcing substrate 40 adheres to the protective layer 65 via the adhesive layer 48 in the region corresponding to the central part 14A of the conversion layer 14.

Figure 15:
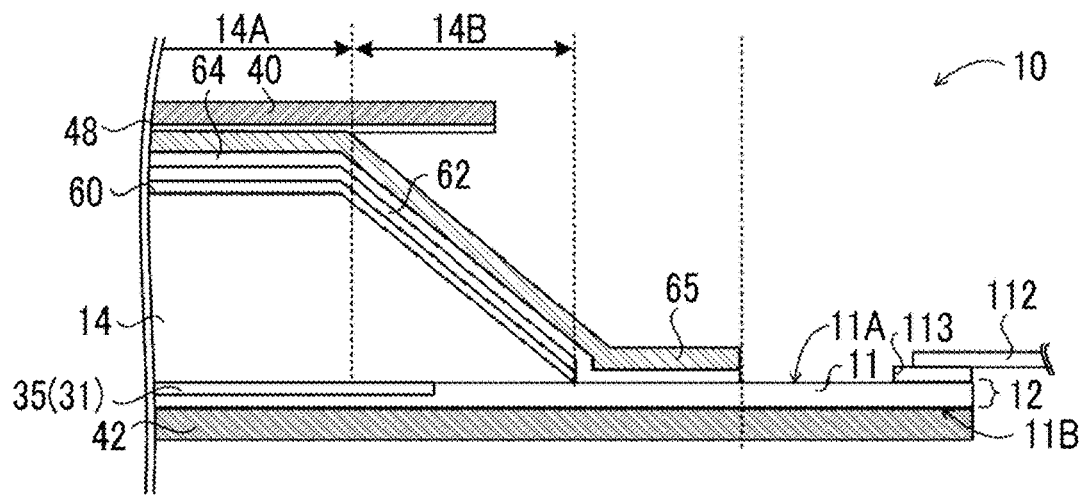
FIG. 15 is a cross-sectional view illustrating an example of a configuration of a radiation detector according to an embodiment of the disclosed technique.

As illustrated in FIG. 15, in a case where the first reinforcing substrate 40 extends to regions corresponding to the central part 14A and the peripheral edge part 14B of the conversion layer 14, the first reinforcing substrate 40 may not have a bent part extending along the inclination at an outer peripheral part of the conversion layer 142. In this case, the first reinforcing substrate 40 adheres to the protective layer 65 via the adhesive layer 48 in the region corresponding to the central part 14A of the conversion layer 14. In the region corresponding to the peripheral edge part 14B of the conversion layer 14, a space corresponding to the inclination of the peripheral edge part 14B of the conversion layer 14 is formed between the conversion layer 14 (protective layer 65) and the first reinforcing substrate 40.

Figure 16:
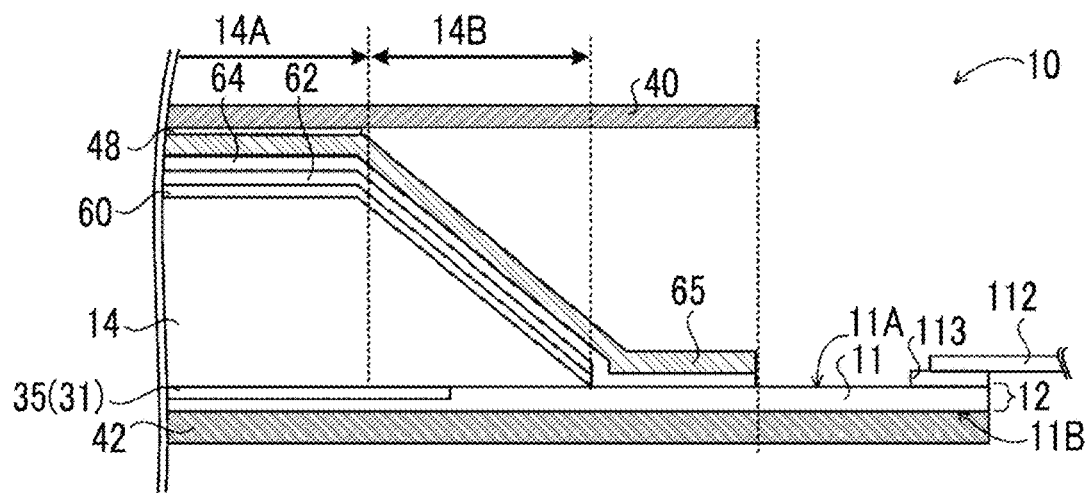
FIG. 16 is a cross-sectional view illustrating an example of a configuration of a radiation detector according to an embodiment of the disclosed technique.

Additionally, as illustrated in FIG. 16, the first reinforcing substrate 40 may be provided such that the end part thereof is disposed outside the end part of the conversion layer 14 and is aligned with the end parts of the adhesive layer 64 and the protective layer 65 extending onto the TFT substrate 12. In addition, it is not necessary that the position of the end part of the first reinforcing substrate 40 and the positions of the end parts of the adhesive layer 64 and the protective layer 65 completely coincide with each other.

In the example illustrated in FIG. 16, the first reinforcing substrate 40 adheres to the protective layer 65 via the adhesive layer 48 in the region corresponding to the central part 14A of the conversion layer 14, and a space corresponding to the inclination of the peripheral edge part 14B of the conversion layer 14 is formed between the conversion layer 14 (protective layer 65) and the first reinforcing substrate 40, in the region corresponding to the peripheral edge part 14B of the conversion layer 14 and the region further outside thereof.

Figure 17:
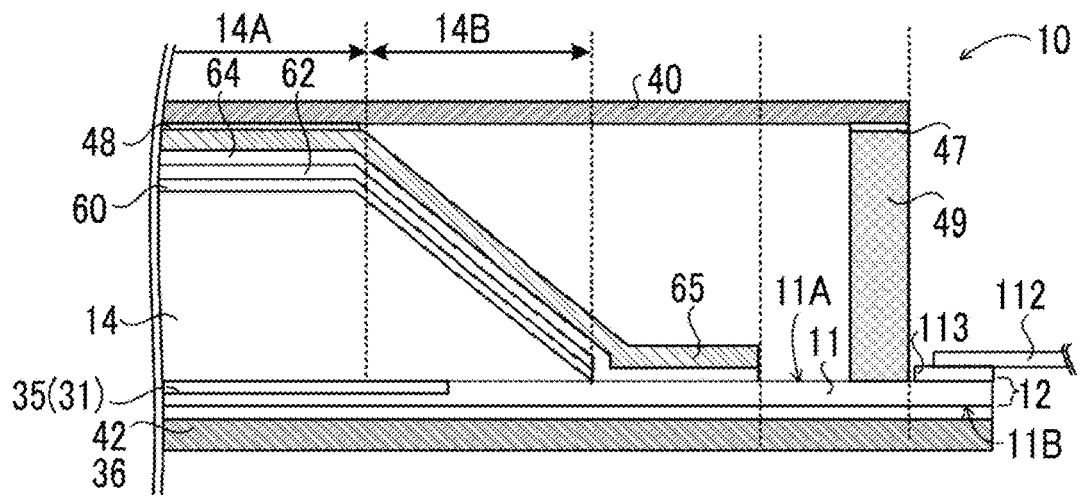
FIG. 17 is a cross-sectional view illustrating an example of a configuration of a radiation detector according to an embodiment of the disclosed technique.
Figure 18:
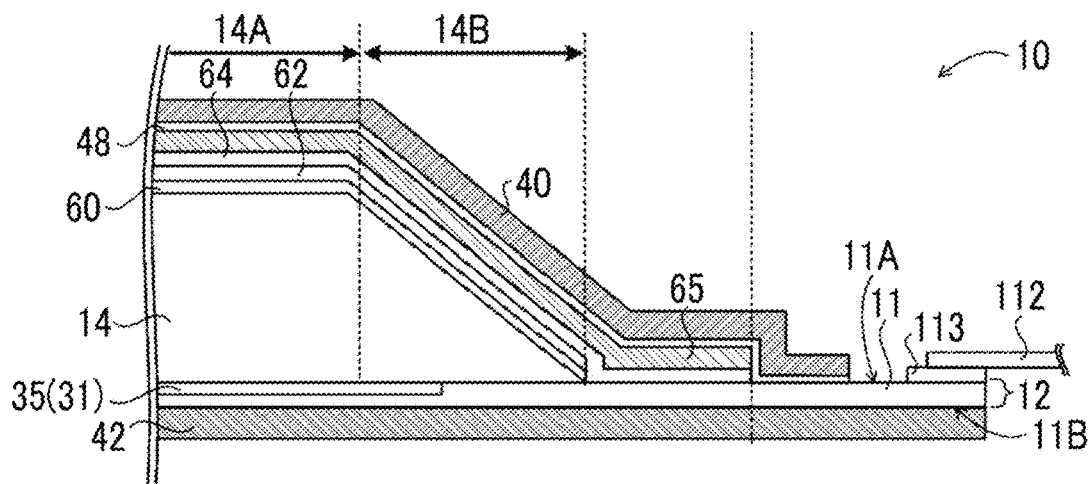
FIG. 18 is a cross-sectional view illustrating an example of a configuration of a radiation detector according to an embodiment of the disclosed technique.

Additionally, as illustrated in FIGS. 17 and 18, the end part of the first reinforcing substrate 40 may be provided to be located outside the end parts of the adhesive layer 64 and the protective layer 65 extending onto the TFT substrate 12 and inside the end part of the TFT substrate 12.

In the example illustrated in FIG. 17, the first reinforcing substrate 40 adheres to the protective layer 65 via the adhesive layer 48 in the region corresponding to the central part 14A of the conversion layer 14, and a space corresponding to the inclination of the peripheral edge part 14B of the conversion layer 14 is formed between the conversion layer 14 (protective layer 65) and the first reinforcing substrate 40 and between the TFT substrate 12 and the first reinforcing substrate 40, in the region corresponding to the peripheral edge part 14B of the conversion layer 14 and the region further outside thereof.

In the example illustrated in FIG. 17, the end part of the first reinforcing substrate 40 is supported by the spacer 49. That is, one end of the spacer 49 is connected to the first surface 11A of the base material 11 of the TFT substrate 12, and the other end of the spacer 49 is connected to the end part of the first reinforcing substrate 40 via the adhesive layer 47. By supporting the end part of the first reinforcing substrate 40 extending while forming a space with the TFT substrate 12 by the spacer 49, the deflection suppressing effect of the first reinforcing substrate 40 up to the vicinity of the end part of the TFT substrate 12 can be exerted.

In the example illustrated in FIG. 18, the outer peripheral part of the first reinforcing substrate 40 is bent in a state along the inclination of the peripheral edge part 14B of the conversion layer 14, and the adhesive layer 64 and the protective layer 65 also cover a portion covering the TFT substrate 12 and the TFT substrate 12 outside thereof. That is, the end parts of the adhesive layer 64 and the protective layer 65 are sealed with the first reinforcing substrate 40. The portion of the first reinforcing substrate 40 extending onto the TFT substrate 12 adheres to the TFT substrate 12 via the adhesive layer 48. By covering the end parts of the adhesive layer 64 and the protective layer 65 with the first reinforcing substrate 40 in this way, it is possible to suppress the peeling of the protective layer 65 in a case where the TFT substrate 12 is deflected in the step of peeling the TFT substrate 12 from the support body 400.

Figure 19:
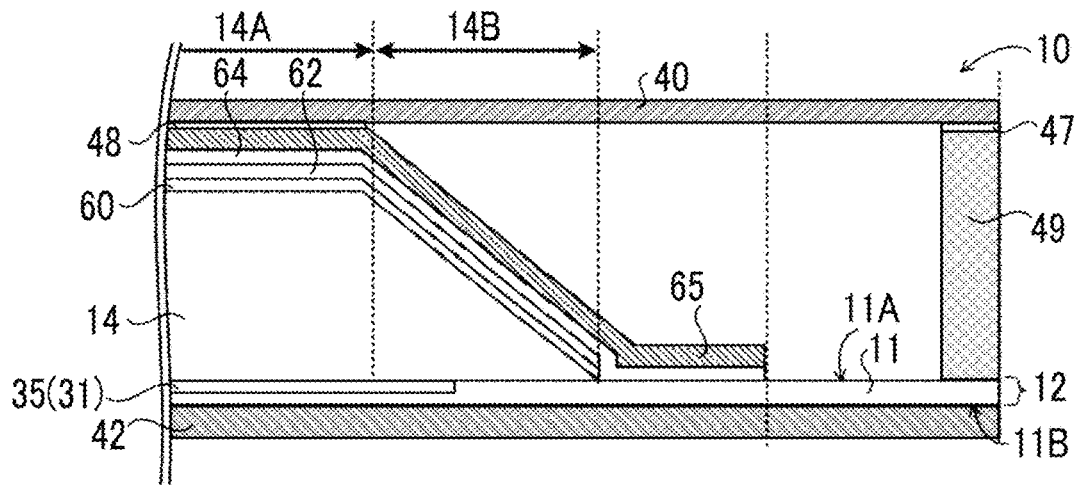
FIG. 19 is a cross-sectional view illustrating an example of a configuration of a radiation detector according to an embodiment of the disclosed technique.
Figure 20:
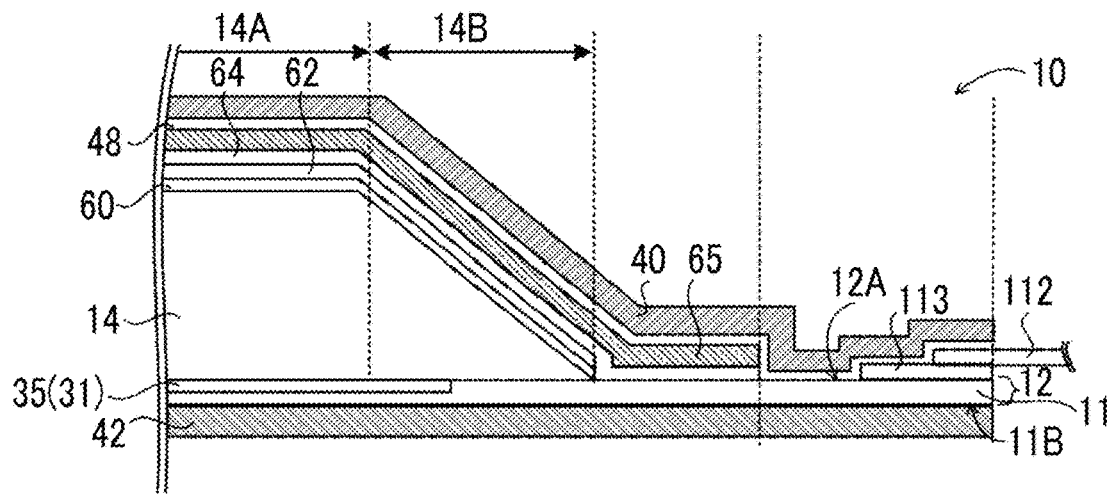
FIG. 20 is a cross-sectional view illustrating an example of a configuration of a radiation detector according to an embodiment of the disclosed technique.

Additionally, as illustrated in FIGS. 19 and 20, the first reinforcing substrate 40 may be provided in a state in which the end part thereof is aligned with the end part of the TFT substrate 12. In addition, it is not necessary that the position of the end part of the first reinforcing substrate 40 and the position of the end part of the TFT substrate 12 completely coincide with each other.

In the example illustrated in FIG. 19, the first reinforcing substrate 40 adheres to the protective layer 65 via the adhesive layer 48 in the region corresponding to the central part 14A of the conversion layer 14, and a space corresponding to the inclination of the peripheral edge part 14B of the conversion layer 14 is formed between the conversion layer 14 (protective layer 65) and the first reinforcing substrate 40 and between the TFT substrate 12 and the first reinforcing substrate 40, in the region corresponding to the peripheral edge part 14B of the conversion layer 14 and the region further outside thereof.

In the example illustrated in FIG. 19, the end part of the first reinforcing substrate 40 is supported by the spacer 49. That is, one end of the spacer 49 is connected to the flexible cable 112 provided at the end part of the TFT substrate 12, and the other end of the spacer 49 is connected to the end part of the first reinforcing substrate 40 via the adhesive layer 47. By supporting the end part of the first reinforcing substrate 40 extending while forming a space with the TFT substrate 12 by the spacer 49, the deflection suppressing effect of the first reinforcing substrate 40 up to the vicinity of the end part of the TFT substrate 12 can be exerted.

Additionally, in a case where the TFT substrate 12 is peeled from the support body 400 after the flexible cable 112 is connected to the terminal 113, the effect of suppressing the poor connection of the flexible cable 112 can be exerted even in a case where the TFT substrate 12 is deflected.

In the example illustrated in FIG. 20, the outer peripheral part of the first reinforcing substrate 40 is bent in a state in which the outer peripheral part extends along the inclination of the peripheral edge part 14B of the conversion layer 14, and the adhesive layer 64 and the protective layer 65 also cover the portion covering the TFT substrate 12, the substrate outside thereof, and the connection part between the terminal 113 and the flexible cable 112. The portions of the first reinforcing substrate 40 extending onto the TFT substrate 12 and the flexible cable 112 respectively adhere to the TFT substrate 12 and the flexible cable 112 via the adhesive layer 48. The connection part between the flexible cable 112 and the terminal 113 is covered with the first reinforcing substrate 40. Accordingly, in a case where the TFT substrate 12 is peeled from the support body 400 after the flexible cable 112 is connected to the terminal 113, the effect of suppressing the poor connection of the flexible cable 112 can be exerted even in a case where the TFT substrate 12 is deflected.

Figure 21:
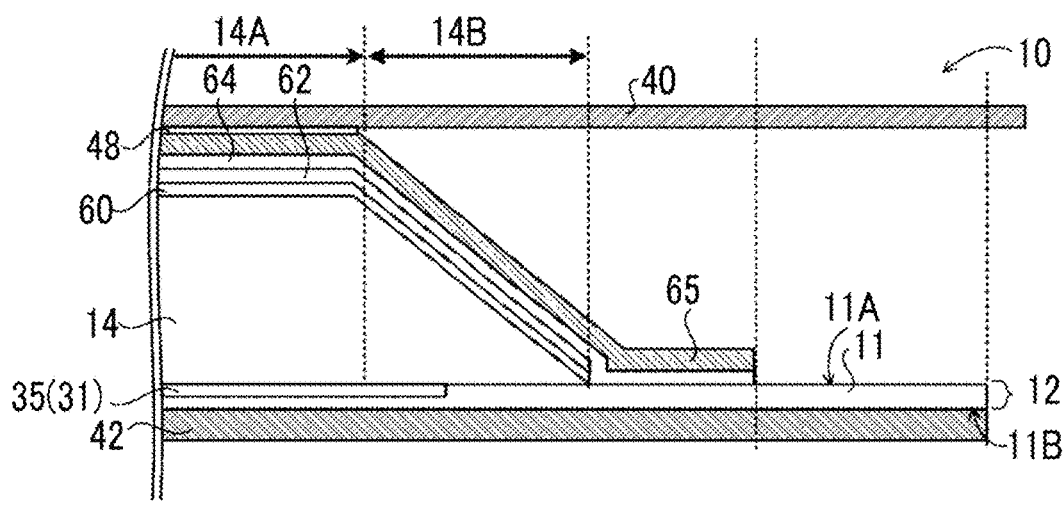
FIG. 21 is a cross-sectional view illustrating an example of a configuration of a radiation detector according to an embodiment of the disclosed technique.
Figure 22:
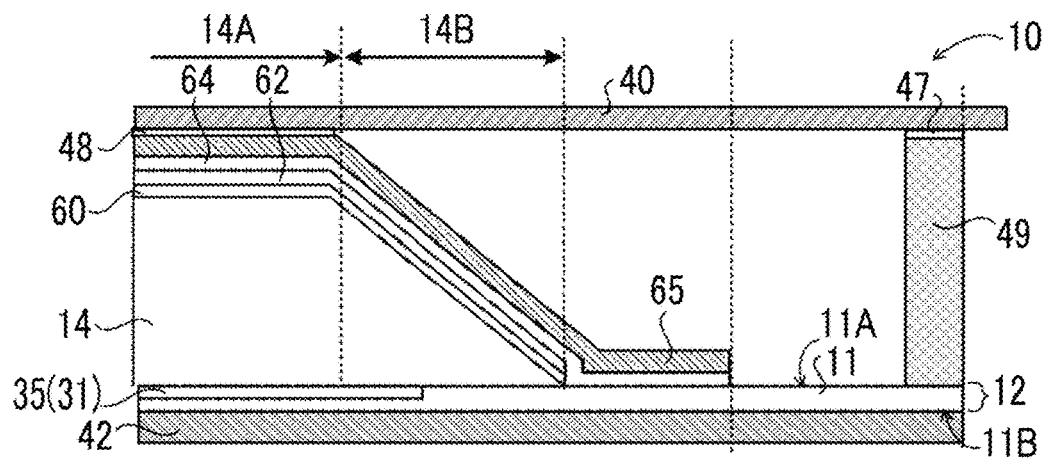
FIG. 22 is a cross-sectional view illustrating an example of a configuration of a radiation detector according to an embodiment of the disclosed technique.
Figure 23:
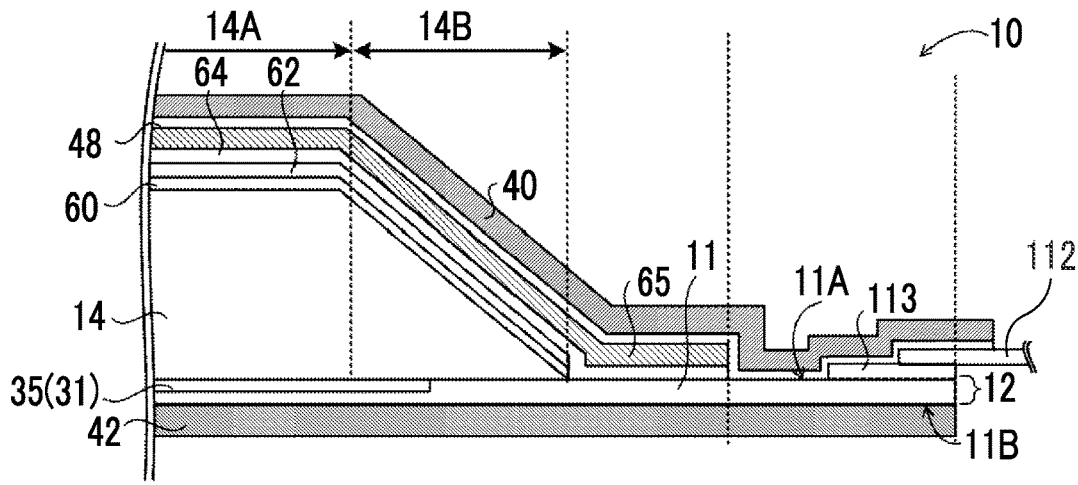
FIG. 23 is a cross-sectional view illustrating an example of a configuration of a radiation detector according to an embodiment of the disclosed technique.

Additionally, as illustrated in FIGS. 21 to 23, the first reinforcing substrate 40 may be provided in a state in which the end part thereof is located outside the end part of the TFT substrate 12.

In the example illustrated in FIG. 21, the first reinforcing substrate 40 adheres to the protective layer 65 via the pressure sensitive adhesive layer 48 in the region corresponding to the central part 14A of the conversion layer 14, and a space corresponding to the inclination of the peripheral edge part 14B of the conversion layer 14 is formed between the conversion layer 14 (protective layer 65) and the first reinforcing substrate 40 and between the TFT substrate 12 and the first reinforcing substrate 40, in the region corresponding to the peripheral edge part 14B of the conversion layer 14 and the region further outside thereof.

In the example illustrated in FIG. 22, the end part of the first reinforcing substrate 40 is supported by the spacer 49. That is, one end of the spacer 49 is connected to the flexible cable 112 provided at the end part of the TFT substrate 12, and the other end of the spacer 49 is connected to the end part of the first reinforcing substrate 40 via the adhesive layer 47. By supporting the end part of the first reinforcing substrate 40 extending while forming a space with the TFT substrate 12 by the spacer 49, the deflection suppressing effect of the first reinforcing substrate 40 up to the vicinity of the end part of the TFT substrate 12 can be exerted.

Additionally, in a case where the TFT substrate 12 is peeled from the support body 400 after the flexible cable 112 is connected to the terminal 113, the effect of suppressing the poor connection of the flexible cable 112 can be exerted even in a case where the TFT substrate 12 is deflected.

In the example illustrated in FIG. 23, the outer peripheral part of the first reinforcing substrate 40 is bent in a state in which the outer peripheral part extends along the inclination of the peripheral edge part 14B of the conversion layer 14, and the adhesive layer 64 and the protective layer 65 also cover the portion covering the TFT substrate 12, the substrate outside thereof, and the connection part between the terminal 113 and the flexible cable 112. The portions of the first reinforcing substrate 40 extending onto the TFT substrate 12 and the flexible cable 112 respectively adhere to the TFT substrate 12 and the flexible cable 112 via the adhesive layer 48. The connection part between the flexible cable 112 and the terminal 113 is covered with the first reinforcing substrate 40. Accordingly, in a case where the TFT substrate 12 is peeled from the support body 400 after the flexible cable 112 is connected to the terminal 113, the effect of suppressing the poor connection of the flexible cable 112 can be exerted even in a case where the TFT substrate 12 is deflected.

Figure 24:
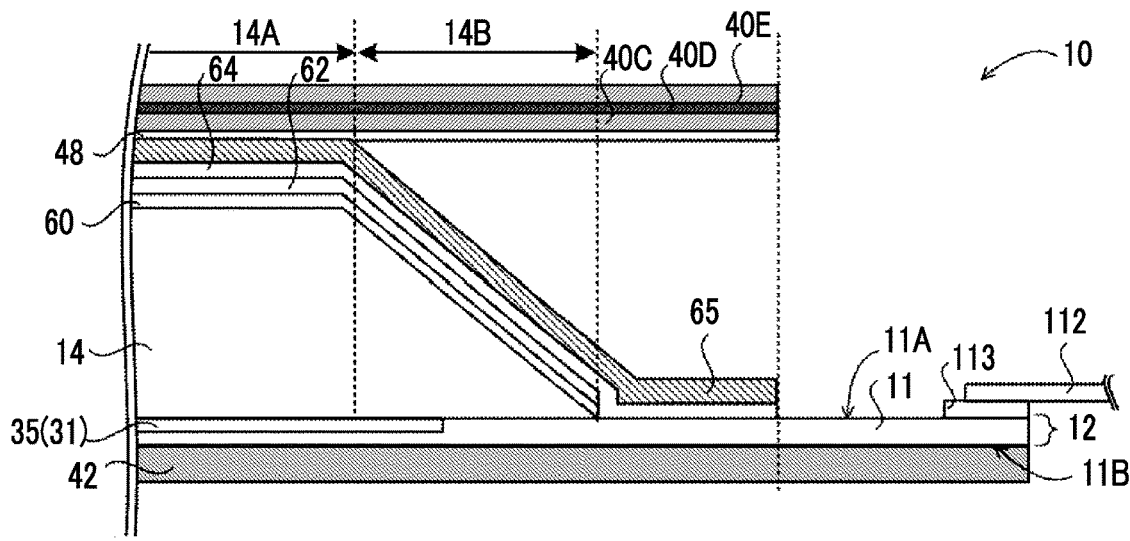
FIG. 24 is a cross-sectional view illustrating an example of a configuration of a radiation detector according to an embodiment of the disclosed technique.

Additionally, the first reinforcing substrate 40 is not limited to a single layer and may be constituted of multiple layers. For example, the example illustrated in FIG. 24 shows a form in which the radiation detector 10 has a three-layer multilayer film in which first reinforcing substrates 40, that is, a first-first reinforcing substrate 40C, a second-first reinforcing substrate 40D, and a third-first reinforcing substrate 40E are laminated in this order from the one closest to the conversion layer 14.

In a case where the first reinforcing substrate 40 has multiple layers, it is preferable that respective layers included in the first reinforcing substrate 40 have different functions. For example, in the example illustrated in FIG. 24, the first reinforcing substrates 40 may be made have an electromagnetic shielding function by using the first-first reinforcing substrate 40C and the third-first reinforcing substrate 40E as layers having a non-conductive antistatic function and using the second reinforcing substrate 40D as a conductive layer. Examples of the first-first reinforcing substrate 40C and the third-first reinforcing substrate 40E in this case include an antistatic film such as a film using antistatic paint "Colcoat" (product name: manufactured by Colcoat Co., Ltd.). Additionally, examples of the second-first reinforcing substrate 40D include a conductive sheet, a conductive mesh sheet such as Cu, and the like.

Figure 25:
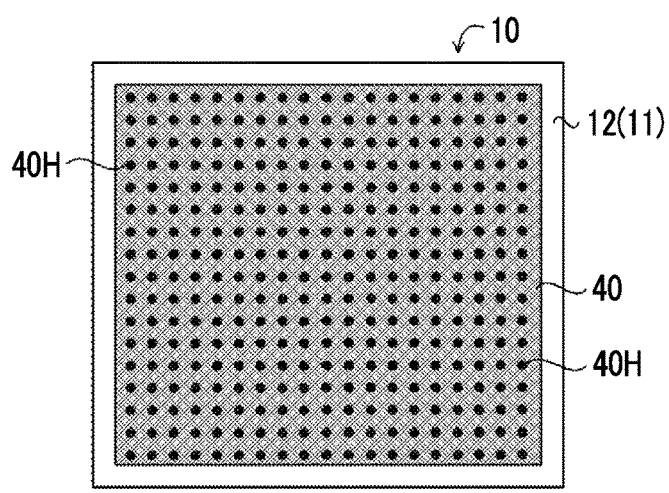
FIG. 25 is a plan view illustrating an example of the structure of the first reinforcing substrate according to the embodiment of the disclosed technique.

Additionally, FIG. 25 is a plan view illustrating an example of the structure of the first reinforcing substrate 40. The first reinforcing substrate 40 may have a plurality of through-holes 40H on a main surface thereof. The size and pitch of the through-holes 40H are determined so that a desired stiffness can be obtained in the first reinforcing substrate 40.

As the first reinforcing substrate 40 has the plurality of through-holes 40H, the air introduced into a joining surface between the first reinforcing substrate 40 and the conversion layer 14 can be discharged from the through-holes 40H. Accordingly, it is possible to suppress the generation of air bubbles on the joining surface between the first reinforcing substrate 40 and the conversion layer 14.

In a case where means for discharging the air introduced into the joining surface between the first reinforcing substrate 40 and the conversion layer 14 is not present, there is a concern that air bubbles may be generated on the joining surface. For example, when the air bubbles generated on the joining surface expand due to the heat generated during the operation of the radiographic imaging apparatus 1, the adhesiveness between the first reinforcing substrate 40 and the conversion layer 14 decreases. Accordingly, there is a concern that the deflection suppressing effect of the first reinforcing substrate 40 may not be sufficiently exhibited. As illustrated in FIG. 25, by using the first reinforcing substrate 40 having the plurality of through-holes 40H, it is possible to suppress the generation of air bubbles on the joining surface between the first reinforcing substrate 40 and the conversion layer 14 as described above. Thus, it is possible to maintain the adhesiveness between the first reinforcing substrate 40 and the conversion layer 14, and it is possible to maintain the deflection suppressing effect of the first reinforcing substrate 40.

Figure 26:
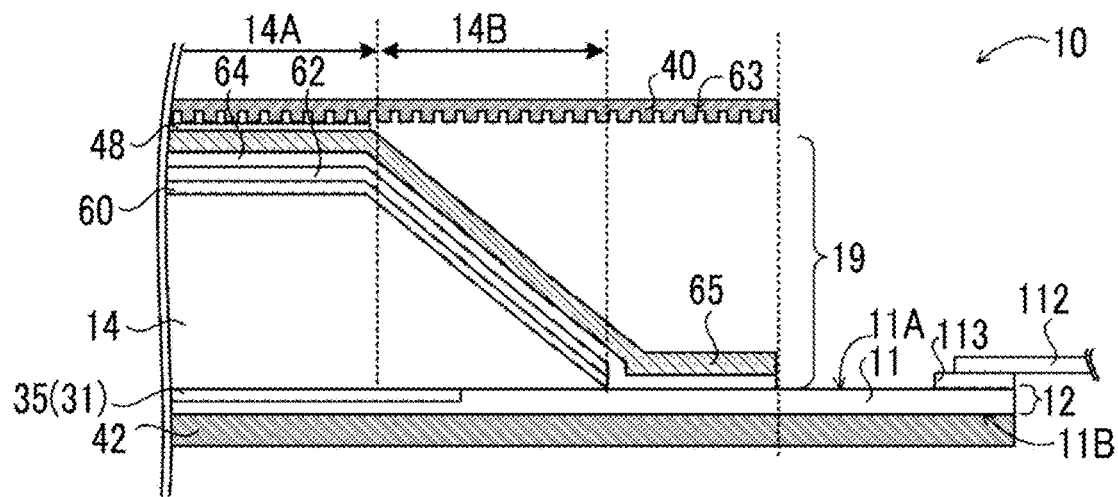
FIG. 26 is a cross-sectional view illustrating an example of a configuration of a radiation detector according to an embodiment of the disclosed technique.
Figure 27:
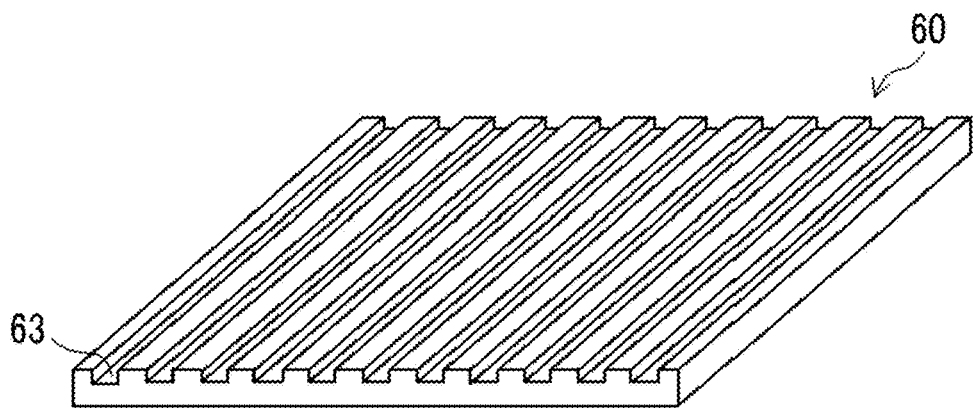
FIG. 27 is a plan view illustrating an example of the structure of a first reinforcing substrate according to the embodiment of the disclosed technique.

FIG. 27 is a perspective view illustrating another example of the structure of the first reinforcing substrate 40. In the example illustrated in FIG. 27, the first reinforcing substrate 40 has an irregular structure on the joining surface with the conversion layer 14. As illustrated in FIG. 27, this irregular structure may be configured to include a plurality of grooves 63 disposed parallel to each other. In the first reinforcing substrate 40, for example, as illustrated in FIG. 26, a surface having the irregular structure formed by the plurality of grooves 63 is joined to the conversion layer 14 covered with the reflective layer 62. In this way, as the first reinforcing substrate 40 has the irregular structure on the joining surface with the conversion layer 14, the air introduced into a joining part between the first reinforcing substrate 40 and the conversion layer 14 can be discharged from the groove 63. Accordingly, similar to the form illustrated in FIG. 25, it is possible to suppress the generation of air bubbles on the joining surface between the first reinforcing substrate 40 and the conversion layer 14. Accordingly, it is possible to maintain the adhesiveness between the first reinforcing substrate 40 and the conversion layer 14, and it is possible to maintain the deflection suppressing effect of the first reinforcing substrate 40.

Figure 28:
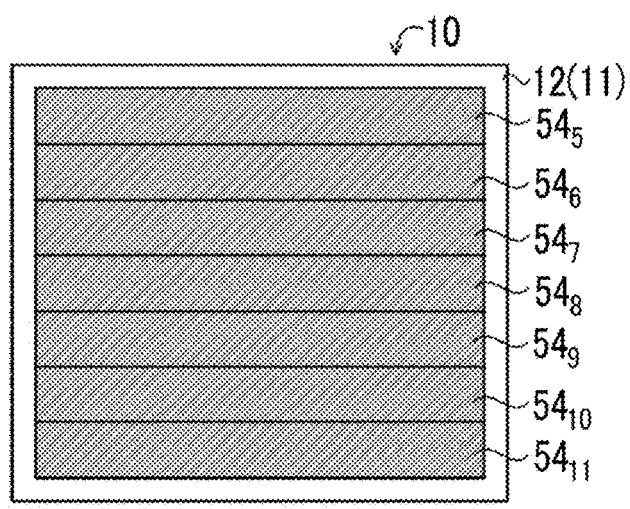
FIG. 28 is a plan view illustrating an example of the structure of the first reinforcing substrate according to the embodiment of the disclosed technique.
Figure 29:
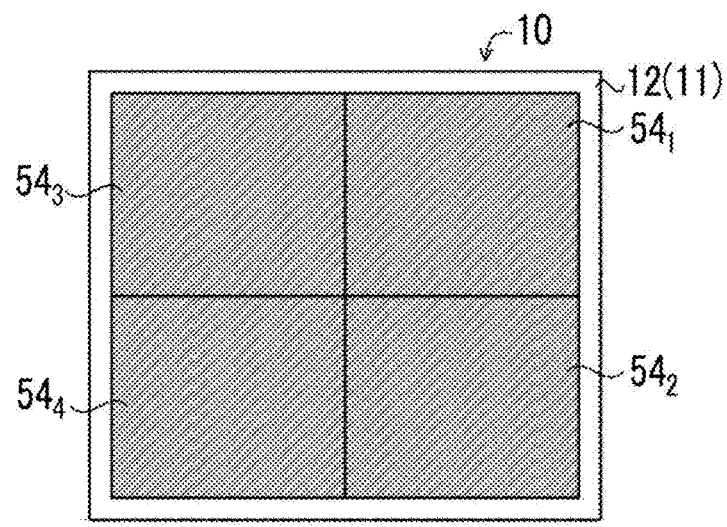
FIG. 29 is a plan view illustrating an example of the structure of the first reinforcing substrate according to the embodiment of the disclosed technique.

FIGS. 28 and 29 are plan views illustrating other examples of the structure of the first reinforcing substrate 40, respectively. As illustrated in FIGS. 28 and 29, the first reinforcing substrate 40 may be divided into a plurality of fragments 54. As illustrated in FIG. 28, the first reinforcing substrate 40 may be divided into the plurality of fragments 54 ($54_5$ to $54_{11}$) so as to be arranged in one direction. Additionally, as illustrated in FIG. 29, the first reinforcing substrate 40 may be divided such that the plurality of fragments 54 ($54_1$ to $54_4$) are arranged in the longitudinal direction and the transverse direction.

As the area of the first reinforcing substrate 40 is larger, air bubbles are more easily generated on the joining surface between the first reinforcing substrate 40 and the conversion layer 14. As illustrated in FIGS. 28 and 29, by dividing the first reinforcing substrate 40 into the plurality of fragments 54, it is possible to suppress the generation of air bubbles on the joining surface between the first reinforcing substrate 40 and the conversion layer 14. Accordingly, it is possible to maintain the adhesiveness between the first reinforcing substrate 40 and the conversion layer 14, and it is possible to maintain the deflection suppressing effect of the first reinforcing substrate 40. Additionally, the effect of facilitating the peeling of the first reinforcing substrate 40 (fragment 54) from the TFT substrate 12 can be obtained.

Figure 30:
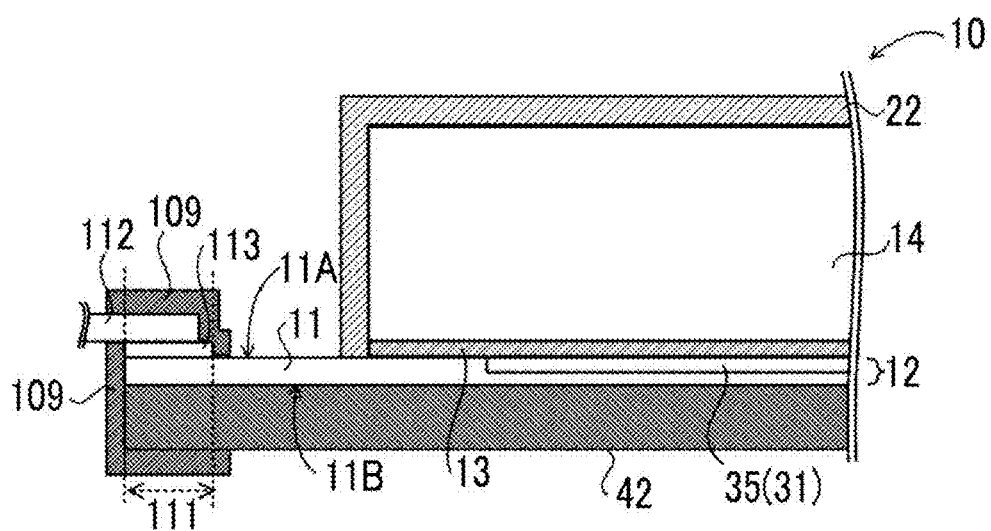
FIG. 30 is a cross-sectional view illustrating another example of the radiation detector of the embodiment.

Additionally, for example, as illustrated in FIG. 30, the radiation detector 10 preferably covers the edge part of the flexible cable 112 with a moistureproof insulating film 109. In the example illustrated in FIG. 30, the moistureproof insulating film 109 covers the entire region of the base material 11 corresponding to the terminal region 111 from above the flexible cable 112 in a state in which the flexible cable 112 is connected to the terminal 113. As the moistureproof insulating film 109, for example, Tuffy (registered trademark), which is a moistureproof insulating material for flat panel display (FPD), can be used.

Additionally, in the radiation detector 10 of each of the present embodiment, a form in which the TFT substrate 12 (base material 11) and the second reinforcing substrate 42 have the same size has been described. However, the TFT substrate 12 and the second reinforcing substrate 42 may have different sizes.

For example, in a case where the radiation detector 10 is applied to the radiographic imaging apparatus 1, the radiation detector 10 may be fixedly used in a housing 120 (refer to FIGS. 7A and 8A) for housing the radiation detector 10. In such a case, for example, as in the example illustrated in FIG. 31A, the second reinforcing substrate 42 may be made larger than the TFT substrate 12 to provide a flap or the like, and a portion such as the flap is used to fix the radiation detector 10. For example, a form may be adopted in which a hole is provided in the flap portion of the second reinforcing substrate 42, and the flap portion is fixed to the housing 120 (refer to FIGS. 7A and 8A) by using a screw penetrating the hole.

Figure 31A:
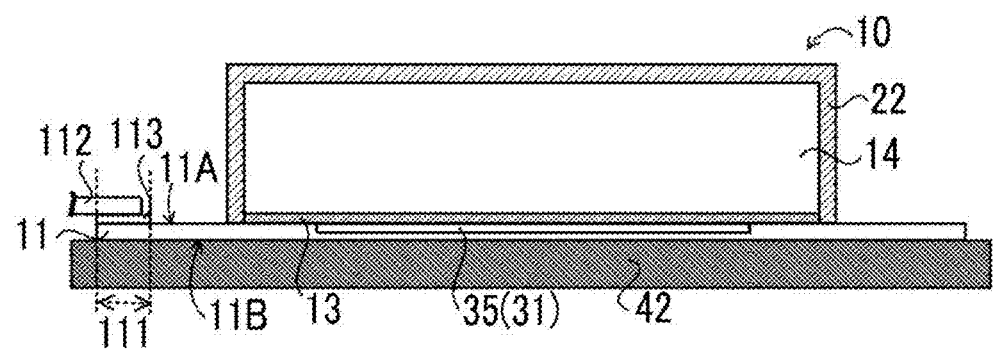
FIG. 31A is a cross-sectional view illustrating an example of a form in which the size of a second reinforcing substrate is different in the radiation detector of the embodiment.
Figure 31B:
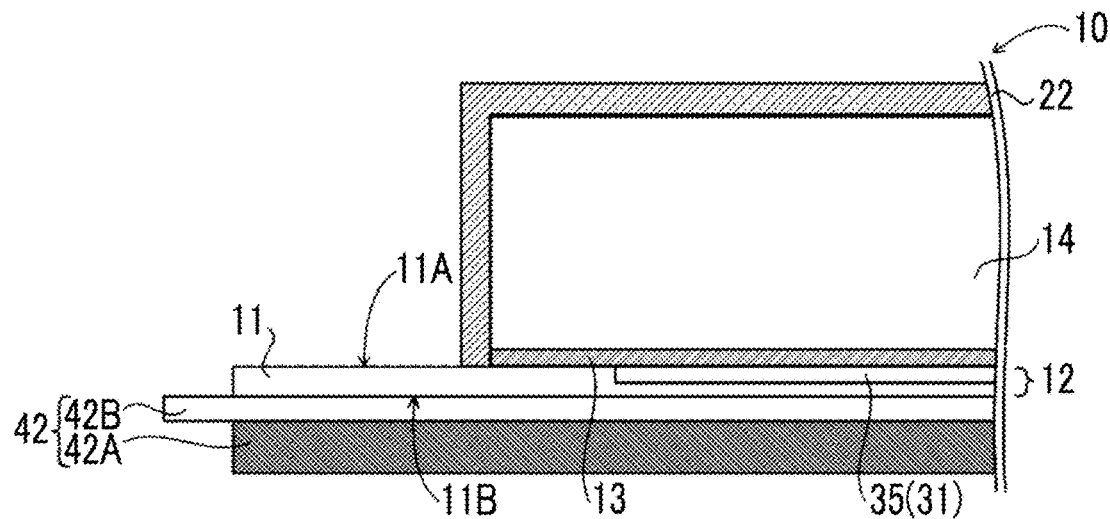
FIG. 31B is a cross-sectional view illustrating an example in which the second reinforcing substrate is constituted of a plurality of layers in the radiation detector of the embodiment.

In addition, the form in which the second reinforcing substrate 42 is made larger than the TFT substrate 12 is not limited to the form illustrated in FIG. 31A. A form may be adopted in which the second reinforcing substrate 42 may be constituted of a plurality of laminated layers and some of the layers is larger than the TFT substrate 12. For example, as illustrated in FIG. 31B, the second reinforcing substrate 42 may have a two-layer structure of a first layer 42A having about the same size as the TFT substrate 12 (base material 11) and a second layer 42B larger than the TFT substrate 12. The first layer 42A and the second layer 42B are bonded to each other with, a double-sided tape, a pressure sensitive adhesive layer, or the like (not illustrated). The first layer 42A is preferably formed of, for example, the same material as the above-described second reinforcing substrate 42 and has the same properties as the second reinforcing substrate 42. Additionally, the second layer 42B is bonded to the second surface 11B of the base material 11 with a double-sided tape, a pressure sensitive adhesive layer, or the like (not illustrated). As the second layer 42B, for example, Alpet (registered trademark) can be applied. Additionally, in a case where the second reinforcing substrate 42 is constituted of the plurality of layers, a form may be adopted in which the first layer 42A is bonded to the second surface 11B of the base material 11 as illustrated in FIG. 31C, contrary to the form illustrated in FIG. 31B.

As described above, in a case where the radiation detector 10 is fixed to the housing 120 (refer to FIGS. 7A and 8A) or the like by using the flap or the like provided on the second reinforcing substrate 42, there is a case where the flap portion is fixed in a bent state. As the thickness of the bent portion is smaller, the flap portion of the second reinforcing substrate 42 is more easily bent, and only the flap portion can be bent without affecting a main body of the radiation detector 10. For that reason, in a case the flap portion or the like is bent, a form is preferable in which the second reinforcing substrate 42 is constituted of the plurality of laminated layers as in the example illustrated in FIGS. 31B and 31C and some of the layers are larger than the TFT substrate 12.

Figure 31C:
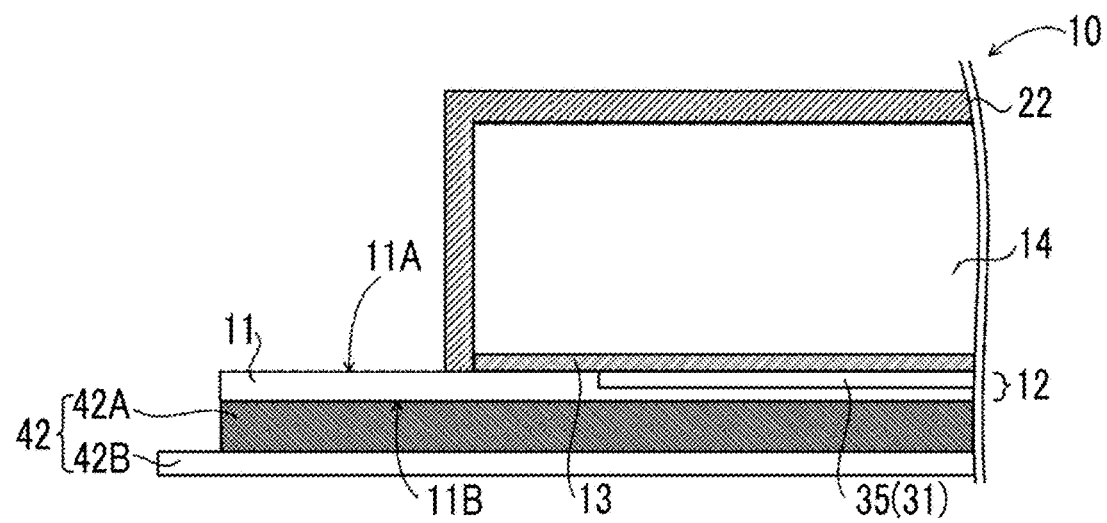
FIG. 31C is a cross-sectional view illustrating another example in which the second reinforcing substrate is constituted of a plurality of layers in the radiation detector of the embodiment.
Figure 32:
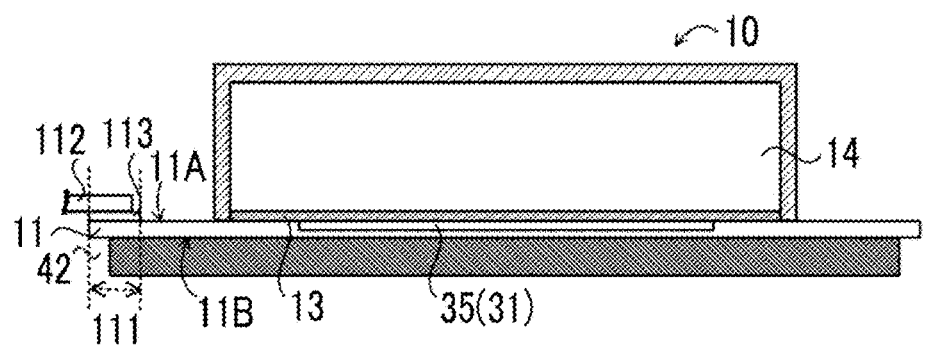
FIG. 32 is a cross-sectional view illustrating another example of a form in which the size of the second reinforcing substrate is different in the radiation detector of the embodiment.

Additionally, as in the example illustrated in FIG. 32, the second reinforcing substrate 42 may be smaller than the TFT substrate 12, contrary to the radiation detector 10 of FIGS. 31A to 31C. Since the end part of the TFT substrate 12 is located outside the end part of the second reinforcing substrate 42, for example, in a case where assembling is performed such that the radiation detector 10 is housed in the housing 120 (refer to FIGS. 7A and 8A), the position of the end part of the TFT substrate 12 can be easily confirmed. Therefore, positioning accuracy can be improved. In addition, not limited to the form illustrated in FIG. 32, as long as at least a part of the end part of the TFT substrate 12 (base material 11) is located outside the second reinforcing substrate 42, the same effects can be obtained, which is preferable.

Additionally, a reinforcing member 52 may be provided on the side of the second reinforcing substrate 42 opposite to the side in contact with the TFT substrate 12 (second surface 11B). FIGS. 33 to 38 are cross-sectional views illustrating examples of the installation form of the reinforcing member 52, respectively.

In the examples illustrated in FIGS. 33 to 37, the reinforcing member 52 is laminated on the surface of the second reinforcing substrate 42 opposite to the surface thereof on the TFT substrate 12 side via the adhesive layer 51. The reinforcing member 52 may be made of the same material as the first reinforcing substrate 40. In a case where the radiation detector 10 is used as the ISS type, the reinforcing member 52 is preferably provided only at the outer peripheral part of the TFT substrate 12 in order to make the area of a portion where the reinforcing member 52 and the pixel region 35 overlap each other as small as possible. That is, as illustrated in FIGS. 33 to 37, the reinforcing member 52 may have an annular shape having an opening 61 in a portion corresponding to the pixel region 35. In this way, by forming a laminated structure with the second reinforcing substrate 42 and the reinforcing member 52 at the outer peripheral part of the TFT substrate 12, the stiffness of the outer peripheral part of the TFT substrate 12 that is relatively easily deflected can be reinforced.

Figure 33:
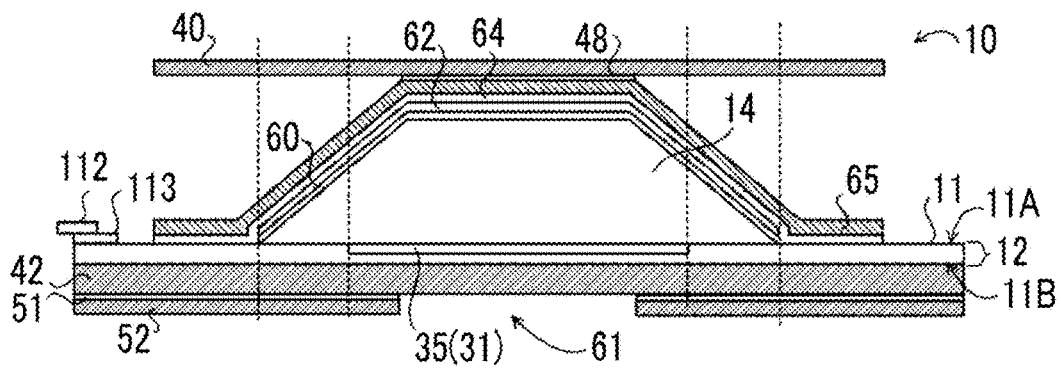
FIG. 33 is a cross-sectional view illustrating an example of a configuration of a radiation detector according to an embodiment of the disclosed technique.
Figure 34:
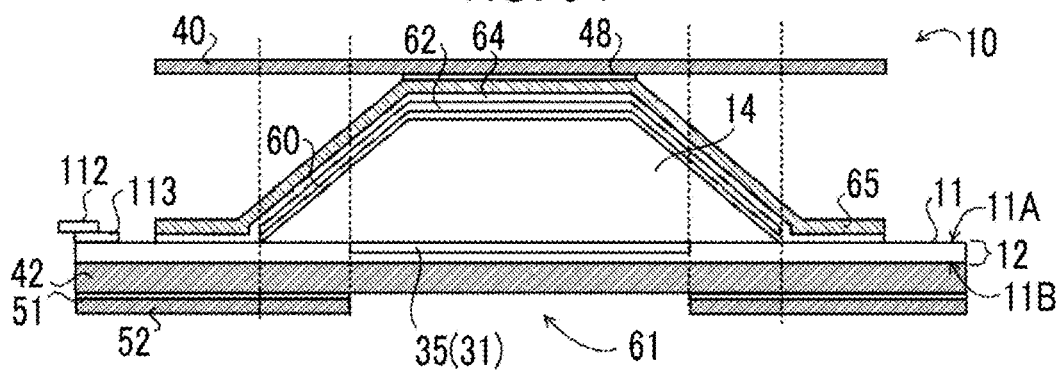
FIG. 34 is a cross-sectional view illustrating an example of a configuration of a radiation detector according to an embodiment of the disclosed technique.
Figure 35:
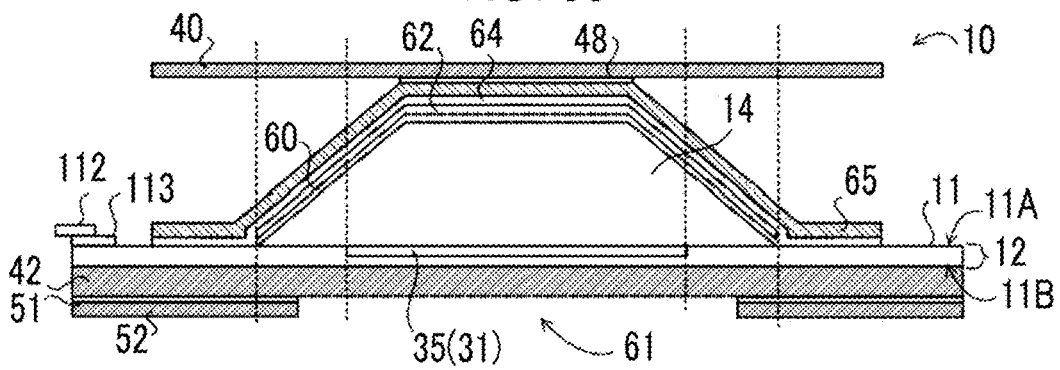
FIG. 35 is a cross-sectional view illustrating an example of a configuration of a radiation detector according to an embodiment of the disclosed technique.

In the examples illustrated in FIGS. 33 to 35, the reinforcing member 52 is provided in the region straddling the end part (outer edge, edge) of the conversion layer 14. In the radiation detector 10, the amount of deflection of the TFT substrate 12 is relatively large at the end part of the conversion layer 14. The effect of suppressing the deflection of the TFT substrate 12 at the end part of the conversion layer 14 can be promoted by forming a laminated structure with the second reinforcing substrate 42 and the reinforcing member 52 in the region corresponding to the end part of the conversion layer 14.

In a case where the radiation detector 10 is used as the ISS type, and as illustrated in FIG. 33, in a case where a part of the reinforcing member 52 overlaps the pixel region 35, there is a concern that an image may be affected depending on the material of the reinforcing member 52. Therefore, in a case where a part of the reinforcing member 52 overlaps the pixel region 35, it is preferable to use plastic as the material of the reinforcing member 52.

As illustrated in FIGS. 34 and 35, a form in which the reinforcing member 52 straddles the end part (outer edge, edge) of the conversion layer 14 and does not overlap the pixel region 35 (that is, a form in which the end part of the opening 61 of the reinforcing member 52 is disposed outside the pixel region 35) is most preferable. In the example illustrated in FIG. 34, the position of the end part of the opening 61 of the reinforcing member 52 and the position of the end part of the pixel region 35 substantially coincide with each other. In the example illustrated in FIG. 35, the end part of the opening 61 of the reinforcing member 52 is disposed between the end part of the pixel region 35 and the end part of the conversion layer 14.

Figure 36:
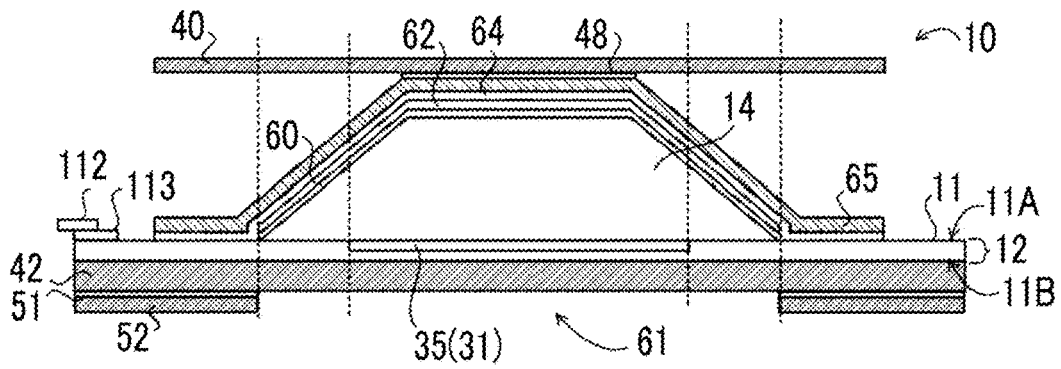
FIG. 36 is a cross-sectional view illustrating an example of a configuration of a radiation detector according to an embodiment of the disclosed technique.
Figure 37:
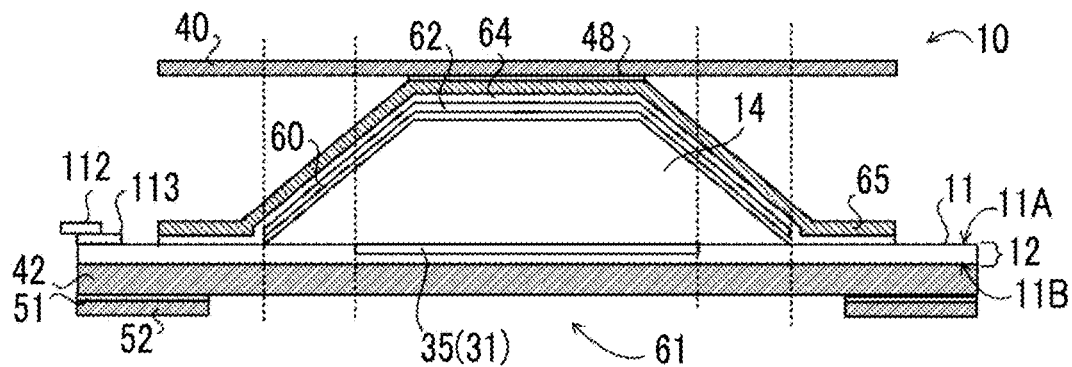
FIG. 37 is a cross-sectional view illustrating an example of a configuration of a radiation detector according to an embodiment of the disclosed technique.

Additionally, the position of the end part of the opening 61 of the reinforcing member 52 may substantially coincide with the position of the end part of the conversion layer 14 as illustrated in FIG. 36, and the conversion layer may be disposed outside the end part of the position of the end part of the conversion layer 14 as illustrated in FIG. 37. In this case, since the reinforcing member 52 does not have a structure that straddles the end part (outer edge, edge) of the conversion layer 14, there is a concern that the effect of suppressing the deflection of the TFT substrate 12 at the end part of the conversion layer 14 may decrease. However, a laminated structure of the second reinforcing substrate 42 and the reinforcing member 52 is formed at the outer peripheral part of the TFT substrate 12 where the connection part between the flexible cable 112 and the terminal 113 is present. Accordingly, the effect of suppressing the deflection of the TFT substrate 12 at the connection part between the flexible cable 112 and the terminal 113 is maintained.

Figure 38:
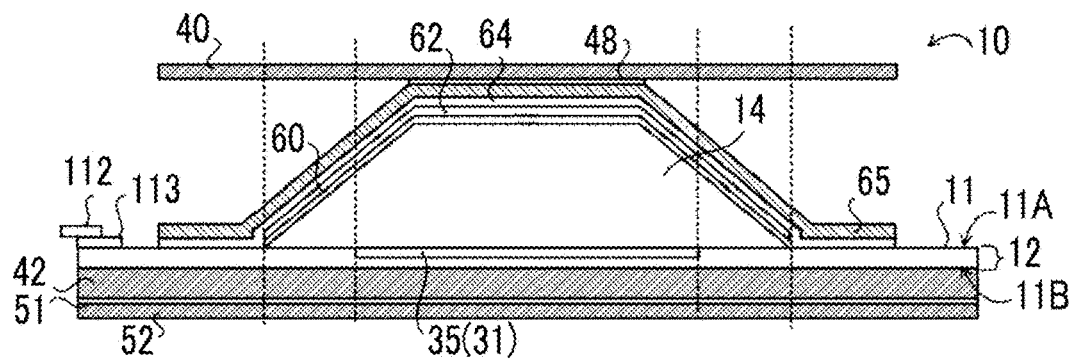
FIG. 38 is a cross-sectional view illustrating an example of a configuration of a radiation detector according to an embodiment of the disclosed technique.

In addition, in a case where the material of the reinforcing member 52 is a material such as carbon that absorbs less radiation, it is possible to suppress that the radiation R reaching the conversion layer 14 decreases because the radiation R is absorbed by the reinforcing member 52 in any of the PSS type and the ISS type. For that reason, as illustrated in FIG. 38, the reinforcing member 52 may have a shape that does not have the opening 61. In other words, the reinforcing member 52 may cover at least a part of the pixel region 35. In addition, the reinforcing member 52 illustrated in FIG. 38 is provided over the entire surface of the second reinforcing substrate 42. The bending modulus of elasticity of the reinforcing member 52 is preferably larger than the bending modulus of elasticity of each of the first reinforcing substrate 40 and the second reinforcing substrate 42. A preferable specific example of the bending modulus of elasticity of the reinforcing member 52 is 8,000 MPa or more.

Figure 39:
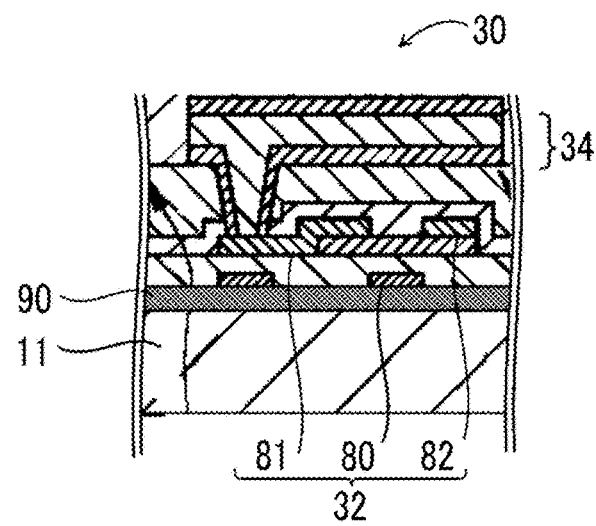
FIG. 39 is a cross-sectional view of one pixel portion of another example of the radiation detector of the embodiment.

Additionally, as in the example illustrated in FIG. 39, it is preferable that a layer 90 made of an inorganic material is provided between the base material 11 and a pixel 30, particularly a gate electrode 80 of the TFT 32 of the pixel 30. Examples of the inorganic material in the case of the example illustrated in FIG. 39 include SiNx, SiOx, and the like. A drain electrode 81 of the TFT 32 and a source electrode 82 are formed in the same layer, and the gate electrode 80 is formed between a layer on which the drain electrode 81 and the source electrode 82 are formed and the base material 11. Additionally, the layer 90 made of the inorganic material is provided between the base material 11 and the gate electrode 80.

Additionally, in the above respective embodiments, as illustrated in FIG. 1, an aspect in which the pixels 30 are two-dimensionally arranged in a matrix has been described. However, the invention is not limited to the aspect, and for example, the pixels 30 may be one-dimensionally arranged or may be arranged in a honeycomb shape. Additionally, the shape of the pixels 30 is also not limited, and may be a rectangular shape, or may be a polygonal shape, such as a hexagonal shape. Moreover, it goes without saying that the shape of the pixel array 31 (pixel region 35) is also not limited.

Additionally, the shape or the like of the conversion layer 14 is not limited to the above respective embodiments. In the above respective embodiments, an aspect in which the shape of the conversion layer 14 is a rectangular shape similar to the shape of the pixel array 31 (pixel region 35) has been described. However, the shape of the conversion layer 14 may not be the same shape as the pixel array 31 (pixel region 35). Additionally, the shape of the pixel array 31 (pixel region 35) may not be a rectangular shape but may be, for example, other polygonal shapes or a circular shape.

In addition, it goes without saying that the configurations, manufacturing methods, and the like of the radiation detectors 10 that are described in the above respective embodiments are merely examples, and can be changed in response to situations without departing from the scope of the present invention.

The disclosure of Japanese Patent Application No. 2019-22119 filed on Feb. 8, 2019 is incorporated in the present specification by reference in its entirety.

All documents, patent applications, and technical standards described in the present specification are incorporated in the present specification by reference in their entireties to the same extent as in a case where the individual documents, patent applications, and technical standards are specifically and individually written to be incorporated by reference.

What is claimed is:

1. A method of manufacturing a radiation detector, the method comprising:
    forming a substrate in which a flexible base material is provided via a peeling layer on a support body and a plurality of pixels that accumulate electric charges generated in response to light converted from radiation are provided in a pixel region of the base material;
    forming a conversion layer for converting the radiation into light on a surface of the base material provided with the pixels;
    providing a first reinforcing substrate on a surface of the conversion layer opposite to a surface on the substrate side;
    peeling the substrate provided with the conversion layer and the first reinforcing substrate from the support body;
    providing a second reinforcing substrate on a surface of the substrate peeled from the support body, the substrate being peeled from the support body; and
    peeling the first reinforcing substrate from the substrate provided with the conversion layer after providing the second reinforcing substrate.

2. The method of manufacturing a radiation detector according to claim 1, further comprising:
    connecting one end of a flexible wiring line connected to a circuit unit for reading out the electric charges accumulated in the plurality of pixels to a terminal region of the substrate before peeling the substrate from the support body.

3. The method of manufacturing a radiation detector according to claim 2, further comprising:
    reworking the wiring line in a state in which the support body or the second reinforcing substrate is provided in a case where a defect occurs in at least one of the wiring line or the circuit unit.

4. The method of manufacturing a radiation detector according to claim 1, further comprising:
    connecting one end of a flexible wiring line connected to a circuit unit for reading out the electric charges accumulated in the plurality of pixels to a terminal region of the substrate before providing the first reinforcing substrate.

5. The method of manufacturing a radiation detector according to claim 1,
    wherein a size of a surface of the first reinforcing substrate on the conversion layer side is smaller than a size of a surface of the base material provided with the pixels.

6. The method of manufacturing a radiation detector according to claim 1,
    wherein a terminal region of the substrate includes a first region covered with the first reinforcing substrate and a second region not covered with the first reinforcing substrate.

7. The method of manufacturing a radiation detector according to claim 6,
    wherein the first region is smaller than the second region.

8. The method of manufacturing a radiation detector according to claim 6,
    wherein a length from one end part on an inner side of the base material to the other end part on an outer edge side of the base material in the first region is ¼ or less of a length from one end part on the inner side of the base material to the other end part on the outer edge side of the base material in the terminal region.

9. The method of manufacturing a radiation detector according to claim 1,
    wherein the first reinforcing substrate is provided with a cutout part at a position corresponding to the terminal region of the substrate.

10. The method of manufacturing a radiation detector according to claim 1, further comprising:
    connecting one end of a flexible wiring line connected to a circuit unit for reading out the electric charges accumulated in the plurality of pixels to a terminal region of the substrate after providing the second reinforcing substrate.

11. The method of manufacturing a radiation detector according to claim 1,
    wherein in peeling the substrate from the support body, the substrate is deflected and peeled from the support body.

12. The method of manufacturing a radiation detector according to claim 1,
    wherein in providing the first reinforcing substrate, the first reinforcing substrate is provided by adhering with a dismantleable adhesive of which adhesiveness is lost by radiation of ultraviolet rays, and
    in peeling the first reinforcing substrate, the first reinforcing substrate is peeled by radiating ultraviolet rays from a surface of the first reinforcing substrate opposite to a surface on the conversion layer side.

13. The method of manufacturing a radiation detector according to claim 1,
    wherein a thickness of the first reinforcing substrate is smaller than a thickness of the second reinforcing substrate.

14. The method of manufacturing a radiation detector according to claim 1,
    wherein the second reinforcing substrate has a higher stiffness than the base material.

15. The method of manufacturing a radiation detector according to claim 1,
    wherein the second reinforcing substrate is a reinforcing substrate formed of a material having a bending modulus of elasticity of 1000 MPa or more and 2500 MPa or less.

16. The method of manufacturing a radiation detector according to claim 1,
    wherein the second reinforcing substrate has a bending stiffness of 540 Pacm$^4$ or more and 140,000 Pacm$^4$ or less.

17. The method of manufacturing a radiation detector according to claim 1,
    wherein a bending stiffness of the second reinforcing substrate is 100 times or more a bending stiffness of the base material.

18. The method of manufacturing a radiation detector according to claim 1, wherein a ratio of a coefficient of thermal expansion of the second reinforcing substrate to a coefficient of thermal expansion of the conversion layer is 0.5 or more and 2 or less.

19. The method of manufacturing a radiation detector according to claim 1,
wherein a size of a surface of the base material facing the second reinforcing substrate is larger than a size of a surface of the second reinforcing substrate facing the base material.

20. The method of manufacturing a radiation detector according to claim 1,
wherein the second reinforcing substrate has a plurality of layers laminated in a lamination direction to be laminated on the substrate, and a size of some of the plurality of layers is larger than a size of a surface of the base material facing the second reinforcing substrate.

21. The method of manufacturing a radiation detector according to claim 1,
wherein a size of a surface of the base material facing the second reinforcing substrate is smaller than a size of a surface of the second reinforcing substrate facing the base material.

22. The method of manufacturing a radiation detector according to claim 1,
wherein at least a part of an end part of the base material is located outside an end part of the second reinforcing substrate.

* * * * *